US012736458B2

(12) United States Patent
Black et al.

(10) Patent No.: US 12,736,458 B2
(45) Date of Patent: Sep. 15, 2026

(54) FLOW CELLS

(71) Applicants: ILLUMINA, INC., San Diego, CA (US); ILLUMINA CAMBRIDGE LIMITED, Cambridge (GB)

(72) Inventors: Hayden Black, San Diego, CA (US); Xavier von Hatten, Cambridge (GB)

(73) Assignees: Illumina, Inc., San Diego, CA (US); Illumina Cambridge Limited, Cambridge (GB)

( * ) Notice: Subject to any disclaimer, the term of this patent is extended or adjusted under 35 U.S.C. 154(b) by 1154 days.

(21) Appl. No.: 17/727,624

(22) Filed: Apr. 22, 2022

(65) Prior Publication Data

US 2022/0364977 A1 Nov. 17, 2022

Related U.S. Application Data

(60) Provisional application No. 63/179,794, filed on Apr. 26, 2021.

(51) Int. Cl.

| | |
|---|---|
| ***G01N 15/1404*** | (2024.01) |
| ***C12Q 1/6869*** | (2018.01) |
| ***C12Q 1/6874*** | (2018.01) |
| ***G01N 33/543*** | (2006.01) |

(52) U.S. Cl.

CPC ....... *G01N 15/1404* (2013.01); *C12Q 1/6869* (2013.01); *C12Q 1/6874* (2013.01); *G01N 33/5438* (2013.01)

(58) Field of Classification Search

CPC ........... G01N 15/1404; G01N 33/5438; C12Q 1/6869; C12Q 1/6874

See application file for complete search history.

(56) References Cited

U.S. PATENT DOCUMENTS

| | | |
|---|---|---|
| 6,713,206 B2 | 3/2004 | Markoski et al. |
| 9,533,305 B2 | 1/2017 | Esfandyarpour et al. |
| 9,758,816 B2 | 9/2017 | Shen et al. |

(Continued)

FOREIGN PATENT DOCUMENTS

| | | | |
|---|---|---|---|
| KR | 101909460 B1 * | 10/2018 | ............ C12Q 1/686 |
| WO | 2021/021515 A1 | 2/2021 | |

OTHER PUBLICATIONS

"Visible Light-Induced Ligation via o-Quinodimethane Thioethers" J. Am. Chem. Soc. 2018, 140, 11848-11854 (Year: 2018).*

(Continued)

*Primary Examiner* — Aaron A Priest
*Assistant Examiner* — Matthew Harold Raymonda
(74) *Attorney, Agent, or Firm* — Dierker & Kavanaugh, P.C.

(57) ABSTRACT

An example method includes introducing a first fluid to a flow channel of a flow cell including a working electrode having a surface that is at least partially exposed to the flow channel, the surface being unmodified or modified with a first member of a transition metal complex binding pair, whereby a linking moiety of a complex present in the first fluid chemically attaches the complex to the surface to form a temporarily modified surface of the working electrode; performing a sensing operation involving the complex of the temporarily modified surface; and applying a desorption voltage of the linking moiety to the working electrode, thereby detaching the linking moiety and regenerating the surface.

9 Claims, 8 Drawing Sheets

Specification includes a Sequence Listing.

(56) References Cited

U.S. PATENT DOCUMENTS

| | | | | |
|---|---|---|---|---|
| 2006/0263033 | A1 | 11/2006 | Lahann et al. | |
| 2011/0203924 | A1 | 8/2011 | Wohlstadter et al. | |
| 2013/0213821 | A1 | 8/2013 | Hanko et al. | |
| 2016/0053252 | A1 | 2/2016 | Von Hatten et al. | |
| 2020/0102609 | A1* | 4/2020 | Glezer | C12Q 1/6869 |

OTHER PUBLICATIONS

Choi et al., "Reusable biosensors via in situ electrochemical surface regeneration in microfluidicapplications", iosensors a ioelectronics, 25(2), 527-531, doi:10.1016/j.bios.2009.08.003, Oct. 15, 2009 (Year: 2009).*

Choi et al., "Reusable biosensors via in situ electrochemical surface regeneration in microfluidic applications", Biosensors and Bioelectronics, 25(2), 527-531, doi:10.1016/j.bios.2009.08.003, Oct. 15, 2009.

Lorenstani et al., "Multi Use Microfluidic Biosensors for Continual Monitoring of Biomarkers from Microphysiological Systems", 2019 20th International Conference on Solid-State Sensors, Actuators and Microsystems & Eurosensors XXXIII (Transducers & Eurosensors XXXIII), 2019, pp. 1036-1039, doi: 10.1109/TRANSDUCERS.2019.8808693, Jun. 23, 2019.

* cited by examiner

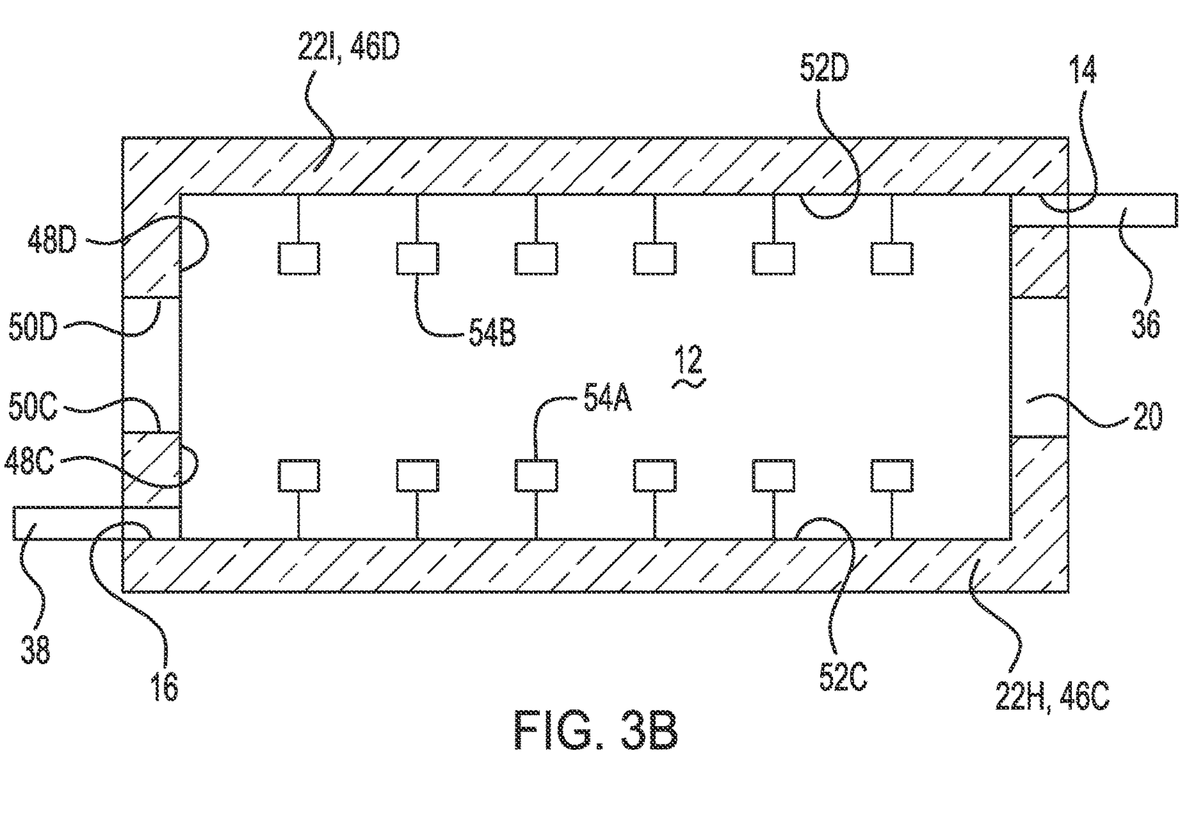
FIG. 3B
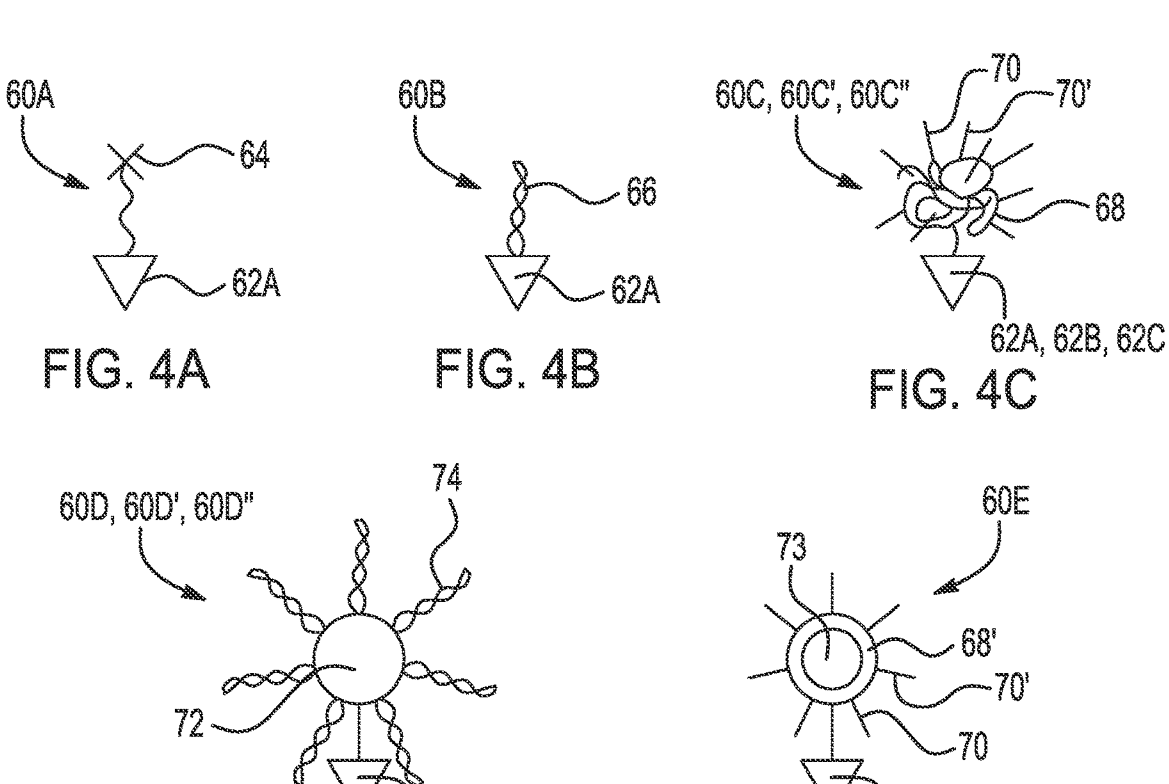
FIG. 4A
FIG. 4B
FIG. 4C
FIG. 4D
FIG. 4E 24A, 24B, 24C
22A, 22B, 22C, 22D, 22E
60C
60D
72
76
62A
70'
70
32A, 32B, 32C
68
32A''', 32B''', 32C'''
1. SENSING OP.
2. ELECTROCHEMICAL DESORPTION 34A, 34B
60C'
60D'
74
62B
32A'''', 32B'''', 32C''''

SEQUENCE LISTING

<160> NUMBER OF SEQ ID NOS: 3

<210> SEQ ID NO 1
<211> LENGTH: 29
<212> TYPE: DNA
<213> ORGANISM: Artificial Sequence
<220> FEATURE:
<223> OTHER INFORMATION: Synthesized

<400> SEQUENCE: 1
aatgatacgg cgaccaccga gauctacac 29

<210> SEQ ID NO 2
<211> LENGTH: 24
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (22)..(22)
<223> OTHER INFORMATION: 8-oxoguanine

<400> SEQUENCE: 2
caagcagaag acggcatacg anat 24

<210> SEQ ID NO 3
<211> LENGTH: 24
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (20)..(20)
<223> OTHER INFORMATION: 8-oxoguanine

<400> SEQUENCE: 3
caagcagaag acggcatacn agat 24

FLOW CELLS

CROSS REFERENCE TO RELATED APPLICATION

This application claims the benefit of U.S. Provisional Application Ser. No. 63/179,794, filed Apr. 26, 2021, the contents of which is incorporated by reference herein in its entirety.

REFERENCE TO SEQUENCE LISTING

The Revised Sequence Listing submitted via EFS-Web is hereby incorporated by reference in its entirety. The name of the file is ILI216B_IP-2117-US_Sequence_Listing_Revised_ST25.txt, the size of the file is 941 bytes, and the date of creation of the file is Jul. 17, 2022.

BACKGROUND

Flow cells are used in a variety of methods and applications, such as gene sequencing, genotyping, etc. For nucleic acid analysis, the surface of the flow cell may be functionalized with specific surface chemistry, such as primers, polymerases, etc. depending upon the reaction that is to take place. In many instances, the surface chemistry is covalently bound to the flow cell surface. Covalent linking may be desirable to maintain the surface chemistry in the active area of the flow cell throughout the lifetime of the flow cell during a variety of uses.

SUMMARY

The flow cells disclosed herein may be used multiple times. The flow cell surface chemistry for nucleic acid analysis is introduced and attached to the surface in real time prior to performing an initial cycle of the analysis (e.g., a sequencing run). The flow cell surface chemistry is also removable, for example, via electrochemically induced desorption or visible light induced dissociation. Upon desorption or dissociation, wash cycle(s) remove the surface chemistry from the flow cell, leaving the surface ready for the introduction of fresh surface chemistry for use in another nucleic acid analysis.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

FIG. 3B is a cross-sectional view taken along line 3B-3B in FIG. 1, of another example of a flow cell having a visible light regenerable surface;

FIG. 4A through FIG. 4E schematically illustrate different examples of complexes that can be used to introduce removable surface chemistry to examples of the flow cell disclosed herein;

DETAILED DESCRIPTION

Figure 1:
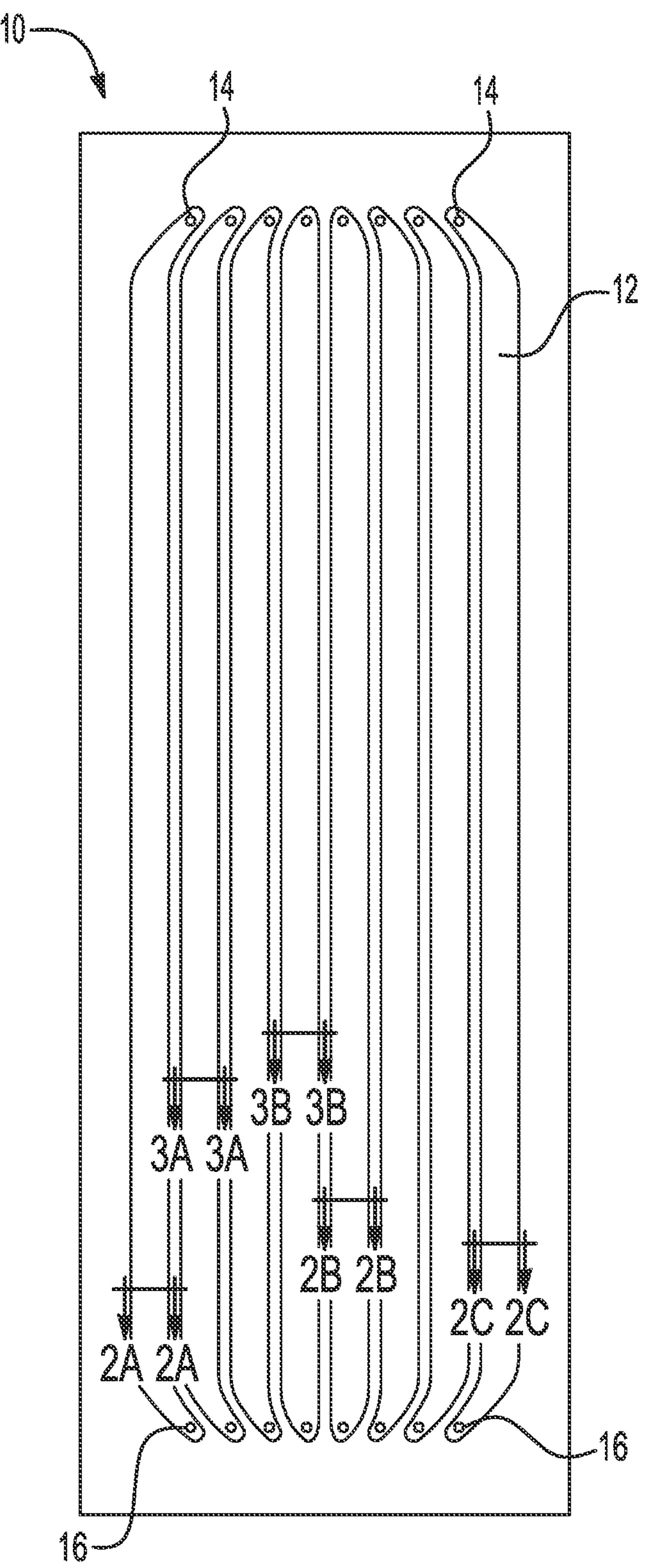
FIG. 1 is a top view of an example of a flow cell.

Disclosed herein are flow cells that may be used multiple times. The initial flow cell surface is unmodified or modified with a first member of a transition metal complex binding pair. Surface chemistry for nucleic acid analysis is introduced into the flow cell and attached to the flow cell surface to generate a temporarily modified surface. After the desired analysis is performed, the surface chemistry is removable from the flow cell. Removal of the surface chemistry regenerates the initial unmodified or modified surface, which prepares the flow cell surface to receive fresh surface chemistry for a subsequent nucleic acid analysis.

The reusability of the flow cell may enable it to be part of the sequencing instrument, as opposed to part of a consumables set.

Definitions

It is to be understood that terms used herein will take on their ordinary meaning in the relevant art unless specified otherwise. Several terms used herein and their meanings are set forth below.

The singular forms "a", "an", and "the" include plural referents unless the context clearly dictates otherwise.

The terms comprising, including, containing and various forms of these terms are synonymous with each other and are meant to be equally broad.

The terms top, bottom, lower, upper, on, etc. are used herein to describe the flow cell and/or the various components of the flow cell. It is to be understood that these directional terms are not meant to imply a specific orientation, but are used to designate relative orientation between components. The use of directional terms should not be interpreted to limit the examples disclosed herein to any specific orientation(s).

The terms first, second, etc. also are not meant to imply a specific orientation or order, but rather are used to distinguish one component from another.

It is to be understood that the ranges provided herein include the stated range and any value or sub-range within the stated range, as if such values or sub-ranges were explicitly recited. For example, a range of about 400 nm to about 1 μm (1000 nm), should be interpreted to include not only the explicitly recited limits of about 400 nm to about 1 μm, but also to include individual values, such as about 708 nm, about 945.5 nm, etc., and sub-ranges, such as from about 425 nm to about 825 nm, from about 550 nm to about 940 nm, etc. Furthermore, when "about" and/or "substantially" are/is utilized to describe a value, they are meant to encompass minor variations (up to +/−10%) from the stated value.

An "acrylamide" is a functional group with the structure

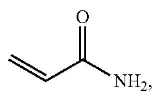

where each H may alternatively be an alkyl, an alkylamino, an alkylamido, an alkylthio, an aryl, a glycol, and optionally substituted variants thereof.

As used herein, "alkyl" refers to a straight or branched hydrocarbon chain that is fully saturated (i.e., contains no double or triple bonds). The alkyl group may have 1 to 20 carbon atoms. Example alkyl groups include methyl, ethyl, propyl, isopropyl, butyl, isobutyl, tertiary butyl, pentyl, hexyl, and the like. As an example, the designation "C1-C6 alkyl" indicates that there are one to six carbon atoms in the alkyl chain, i.e., the alkyl chain is selected from the group consisting of methyl, ethyl, propyl, iso-propyl, n-butyl, isobutyl, sec-butyl, t-butyl, pentyl, and hexyl.

As used herein, "alkylamino" refers to an alkyl group in which one or more of the hydrogen atoms are replaced by an amino group, where the amino group refers to an $—NR_aR_b$ group, where $R_a$ and $R_b$ are each independently selected from a C1-C6 alkyl, C2-C6 alkenyl, C2-C6 alkynyl, C3-C7 carbocycle, C6-C10 aryl, a 5-10 membered heteroaryl, and a 5-10 membered heterocycle.

As used herein, "alkylamido" refers to an alkyl group in which one or more of the hydrogen atoms are replaced by a C-amido group or an N-amido group. A "C-amido" group refers to a "$—C(═O)N(R_aR_b)$" group in which $R_a$ and $R_b$ can independently be selected from the group consisting of alkyl, alkenyl, alkynyl, cycloalkyl, cycloalkenyl, cycloalkynyl, aryl, heteroaryl, heteroalicycle, aralkyl, or (heteroalicyclic)alkyl. An "N-amido" group refers to a "$RC(═O)N(R_a)—$" group in which R and $R_a$ can independently be selected from the group consisting of alkyl, alkenyl, alkynyl, cycloalkyl, cycloalkenyl, cycloalkynyl, aryl, heteroaryl, heteroalicycle, aralkyl, or (heteroalicyclic)alkyl. Any alkylamido may be substituted or unsubstituted.

As used herein, "alkylthio" refers to RS—, in which R is an alkyl. The alkylthio can be substituted or unsubstituted.

As used herein, "alkene" or "alkenyl" refers to a straight or branched hydrocarbon chain containing one or more double bonds. The alkenyl group may have 2 to 20 carbon atoms. Example alkenyl groups include ethenyl, propenyl, butenyl, pentenyl, hexenyl, and the like.

As used herein, "alkyne" or "alkynyl" refers to a straight or branched hydrocarbon chain containing one or more triple bonds. The alkynyl group may have 2 to 20 carbon atoms.

As used herein, "aralkyl" and "aryl(alkyl)" refer to an aryl group connected, as a substituent, via a lower alkylene group. The lower alkylene and aryl group of an aralkyl may be substituted or unsubstituted. Examples include but are not limited to benzyl, 2-phenylalkyl, 3-phenylalkyl, and naphthylalkyl.

The term "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms. Examples of aryl groups include phenyl, naphthyl, azulenyl, and anthracenyl. Any aryl may be a heteroaryl, with at least one heteroatom, that is, an element other than carbon (e.g., nitrogen, oxygen, sulfur, etc.), in ring backbone.

As used herein, the term "attached" refers to the state of two things being joined, fastened, adhered, connected or bound to each other, either directly or indirectly. For example, a nucleic acid can be attached to a functionalized polymer by a covalent or non-covalent bond. A covalent bond is characterized by the sharing of pairs of electrons between atoms. A non-covalent bond is a physical bond that does not involve the sharing of pairs of electrons and can include, for example, hydrogen bonds, ionic bonds, van der Waals forces, hydrophilic interactions and hydrophobic interactions.

An "azide" or "azido" functional group refers to $—N_3$.

As used herein, "carbocycle" means a non-aromatic cyclic ring or ring system containing only carbon atoms in the ring system backbone. When the carbocycle is a ring system, two or more rings may be joined together in a fused, bridged or spiro-connected fashion. Carbocycles may have any degree of saturation, provided that at least one ring in a ring system is not aromatic. Thus, carbocycles include cycloalkyls, cycloalkenyls, and cycloalkynyls. The carbocycle group may have 3 to 20 carbon atoms. Examples of carbocycle rings include cyclopropyl, cyclobutyl, cyclopentyl, cyclohexyl, cyclohexenyl, 2,3-dihydro-indene, bicyclo[2.2.2]octanyl, adamantyl, and spiro[4.4]nonanyl. Any of the carbocycles may be heterocycles, with at least one heteroatom in ring backbone.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s). In some examples, cycloalkyl groups can contain 3 to 8 atoms in the ring(s). A cycloalkyl group may be unsubstituted or substituted. Example cycloalkyl groups include cyclopropyl, cyclobutyl, cyclopentyl, cyclohexyl, cycloheptyl, and cyclooctyl.

As used herein, "cycloalkenyl" or "cycloalkene" means a carbocycle ring or ring system having at least one double bond, wherein no ring in the ring system is aromatic. Examples include cyclohexenyl or cyclohexene and norbornenyl or norbornene.

As used herein, "cycloalkynyl" or "cycloalkyne" means a carbocycle ring or ring system having at least one triple bond, wherein no ring in the ring system is aromatic. An example is cyclooctyne. Another example is bicyclononyne. Still another example is dibenzocyclooctyne (DBCO).

The term "depositing," as used herein, refers to any suitable application technique, which may be manual or automated, and, in some instances, results in modification of the surface properties. Generally, depositing may be performed using vapor deposition techniques, coating techniques, grafting techniques, or the like. Some specific examples include chemical vapor deposition (CVD), spray coating (e.g., ultrasonic spray coating), spin coating, dunk or dip coating, doctor blade coating, puddle dispensing, flow through coating, aerosol printing, screen printing, microcontact printing, inkjet printing, or the like.

As used herein, the term "depression" refers to a discrete concave feature in a substrate or a patterned material having a surface opening that is at least partially surrounded by interstitial region(s) of the substrate or the patterned material. Depressions can have any of a variety of shapes at their opening in a surface including, as examples, round, elliptical, square, polygonal, star shaped (with any number of vertices), etc. The cross-section of a depression taken orthogonally with the surface can be curved, square, polygonal, hyperbolic, conical, angular, etc. As examples, the depression can be a well or two interconnected wells. The depression may also have more complex architectures, such as ridges, step features, etc.

The term "each," when used in reference to a collection of items, is intended to identify an individual item in the collection, but does not necessarily refer to every item in the collection. Exceptions can occur if explicit disclosure or context clearly dictates otherwise.

As used herein, the term "flow cell" is intended to mean a vessel having a flow channel that is in fluid communication with at least one unmodified surface or at least one surface modified with a first member of a transition metal complex binding pair. The unmodified or modified surface is capable of attaching surface chemistry that to be used during a nucleic acid analysis, and is capable of releasing the surface chemistry either electrochemically or upon exposure to visible light. The flow cell also includes an inlet for delivering reagent(s) to the flow channel and an outlet for removing reagent(s) from the flow channel. The flow cell enables the detection of the reactions involving the surface chemistry. For example, the flow cell may include one or more transparent surfaces, which allow for the optical detection of arrays, optically labeled molecules, or the like within the flow channel.

As used herein, a "flow channel" or "channel" may be an area defined between two bonded components, which can selectively receive a liquid sample. In some examples, the flow channel may be defined between a patterned or non-patterned structure and a lid. In other examples, the flow channel may be defined between two patterned or non-patterned structures that are bonded together.

As used herein, "heteroalicyclic" or "heteroalicycle" refers to three-, four-, five-, six-, seven-, eight-, nine-, ten-, up to 18-membered monocyclic, bicyclic, and tricyclic ring system wherein carbon atoms together with from 1 to 5 heteroatoms constitute said ring system. A heteroalicyclic ring system may optionally contain one or more unsaturated bonds situated in such a way, however, that a fully delocalized pi-electron system does not occur throughout all the rings. The heteroatoms are independently selected from oxygen, sulfur, and nitrogen. A heteroalicyclic ring system may further contain one or more carbonyl or thiocarbonyl functionalities, so as to make the definition include oxo-systems and thio-systems such as lactams, lactones, cyclic imides, cyclic thioim ides, and cyclic carbamates. The rings may be joined together in a fused fashion. Additionally, any nitrogens in a heteroalicyclic may be quaternized. Heteroalicycle or heteroalicyclic groups may be unsubstituted or substituted. Examples of such "heteroalicyclic" or "heteroalicycle" groups include 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline, 3,4-methylenedioxyphenyl).

A "(heteroalicyclic)alkyl" refers to a heterocyclic or a heteroalicyclic group connected, as a substituent, via a lower alkylene group. The lower alkylene and heterocycle or a heterocycle of a (heteroalicyclic)alkyl may be substituted or unsubstituted. Examples include tetrahydro-2H-pyran-4-yl) methyl, (piperidin-4-yl)ethyl, (piperidin-4-yl)propyl, (tetrahydro-2H-thiopyran-4-yl)methyl, and (1,3-thiazinan-4-yl) methyl.

As used herein, "hydroxy" or "hydroxyl" refers to an —OH group.

The term "glycol" refers to the end group $—(CH_2)_nOH$, where n ranges from 2 to 10. As specific examples, the glycol may be an ethylene glycol end group $—CH_2CH_2OH$, a propylene glycol end group $—CH_2CH_2CH_2OH$, or a butylene glycol end group $—CH_2CH_2CH_2CH_2OH$.

As used herein, the term "interstitial region" refers to an area, e.g., of a substrate, patterned resin, or other support that separates depressions. For example, an interstitial region can separate one depression of an array from another depression of the array. The two depressions that are separated from each other can be discrete, i.e., lacking physical contact with each other. In many examples, the interstitial region is continuous whereas the depressions are discrete, for example, as is the case for a plurality of depressions defined in an otherwise continuous surface. In other examples, the interstitial regions and the features are discrete, for example, as is the case for a plurality of trenches separated by respective interstitial regions. The separation provided by an interstitial region can be partial or full separation. Interstitial regions may have a surface material that differs from the surface material of the depressions defined in the surface. For example, the depression surface can be an electrode, and the interstitial regions can be an electrically insulating material.

As used herein, a "nucleotide" includes a nitrogen containing heterocyclic base, a sugar, and one or more phosphate groups. Nucleotides are monomeric units of a nucleic acid sequence. In ribonucleic acids (RNA), the sugar is a ribose, and in deoxyribonucleic acids (DNA), the sugar is a deoxyribose, i.e. a sugar lacking a hydroxyl group that is present at the 2' position in ribose. The nitrogen containing heterocyclic base (i.e., nucleobase) can be a purine base or a pyrimidine base. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose is bonded to N-1 of a pyrimidine or N-9 of a purine. A nucleic acid analog may have any of the phosphate backbone, the sugar, or the nucleobase altered. Examples of nucleic acid analogs include, for example, universal bases or phosphate-sugar backbone analogs, such as peptide nucleic acid (PNA).

Figure 2A:
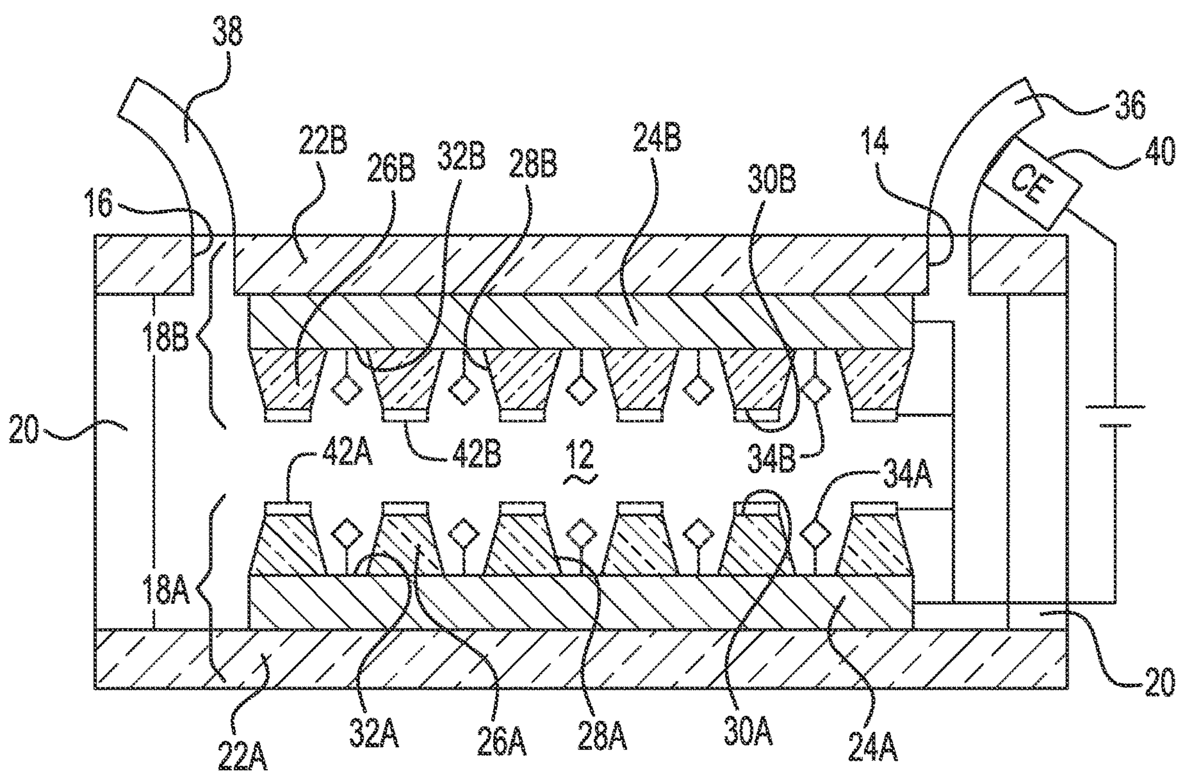
FIG. 2A is a cross-sectional view taken along line 2A-2A in FIG. 1, of an example of a flow cell having an electrochemically regenerable surface.

In some examples, the term "over" may mean that one component or material is positioned directly on another component or material. When one is directly on another, the two are in contact with each other. In FIG. 2A, the working electrode 24A is applied over the substrate 22A so that it is directly on and in contact with the substrate 22A. Similarly, in FIG. 2A, the working electrode 24B is applied over the substrate 22B so that it is directly on and in contact with the substrate 22B.

In other examples, the term “over” may mean that one component or material is positioned indirectly on another component or material. By indirectly on, it is meant that a gap or an additional component or material may be positioned between the two components or materials. In FIG. 2A, the patterned insulating layer 26A is positioned over the substrate 22A such that the two are in indirect contact. More specifically, the patterned insulating layer 26A is indirectly on the substrate 22A because the working electrode 24A is positioned between the two components 26A, 22A.

As used herein, the term “primer” is defined as a single stranded nucleic acid sequence (e.g., single strand DNA). Some primers are part of a primer set, which serve as a starting point for template amplification and cluster generation. Other primers, referred to herein as sequencing primers, serve as a starting point for DNA synthesis. The 5' terminus of a primer set may be modified to allow a coupling reaction with a functional group of one of the orthogonal polymers. The primer length can be any number of bases long and can include a variety of non-natural nucleotides. In an example, the sequencing primer is a short strand, ranging from 10 to 60 bases, or from 20 to 40 bases.

The term “substrate” refers to a structure upon which various components of the flow cell (e.g., electrode(s), a first member of a transition metal complex binding pair, etc.) may be added. The substrate may be a wafer, a panel, a rectangular sheet, a die, or any other suitable configuration. The substrate is generally rigid and is insoluble in an aqueous liquid. The substrate may be a single layer structure, or a multi-layered structure (e.g., including a support and a patterned material on the support). Examples of suitable substrates will be described further herein.

As used herein, the terms “tetrazine” and “tetrazinyl” refer to six-membered heteroaryl group comprising four nitrogen atoms. Tetrazine can be optionally substituted.

The term “transition metal complex binding pair” refers to two agents (one of which is a transition metal complex) that are capable of attaching to one another.

The term “transparent” refers to a material, e.g., in the form of a substrate, electrode, or other layer, that is transparent to a particular wavelength or range of wavelengths. For example, the material may be transparent to excitation and emission wavelength(s) used during nucleic acid analysis. The emission wavelengths are dependent upon the fluorescent dye(s) used in the nucleic acid analysis, and thus a transparent material that is used also depends, in part, upon the fluorescent dye(s). Transparency may be quantified using transmittance, i.e., the ratio of light energy falling on a body to that transmitted through the body. The transmittance of a material will depend upon the thickness of the material and the wavelength of light. In the examples disclosed herein, the transmittance of the material may range from 0.25 (25%) to 1 (100%). The material may be a pure material, a material with some impurities, or a mixture of materials, as long as the resulting substrate, electrode, or other layer is capable of the desired transmittance. Additionally, depending upon the transmittance of the material, the time for light exposure and/or the output power of the light source may be increased or decreased to deliver a suitable dose of light energy through the transparent material to achieve the desired effect (e.g., excite fluorescent labels).

Flow Cells

A flow cell 10 is shown in FIG. 1 from a top view. The flow cell 10 may include two patterned structures bonded together (see, e.g., FIG. 2A and FIG. 3A), two non-patterned structures bonded together (see, e.g., FIG. 2C and FIG. 3B), or one patterned or non-patterned structure bonded to a lid (see, e.g., FIG. 2B). FIG. 1 depicts a top view of the flow cell 10, and thus depicts a surface of a substrate or a surface of the lid. The substrate or lid is transparent to excitation and emission wavelength(s) used during nucleic acid analysis.

Between the two patterned or non-patterned structures or the one patterned or non-patterned structure and the lid is a flow channel 12. The example shown in FIG. 1 includes eight flow channels 12. While eight flow channels 12 are shown, it is to be understood that any number of flow channels 12 may be included in the flow cell 10 (e.g., a single flow channel 12, four flow channels 12, etc.). Each flow channel 12 may be isolated from another flow channel 12 so that fluid introduced into a flow channel 12 does not flow into adjacent flow channel(s) 12. Some examples of the fluids introduced into the flow channel 12 may introduce surface chemistry components (e.g., hydrogels, primers for capture/amplification, particles having a cluster of template nucleic acid strands thereon, etc.), washing solutions, deblocking agents, etc.

The flow channel 12 may have any desirable shape. In an example, the flow channel 12 has a substantially rectangular configuration. The length of the flow channel 12 depends, in part, upon the size of the substrate upon which the patterned or non-patterned structure is formed. The width of the flow channel 12 depends, in part, upon the size of the substrate upon which the patterned or non-patterned structure is formed, the desired number of flow channels 12, the desired space between adjacent channels 12, and the desired space at a perimeter of the patterned or non-patterned structure.

The depth of the flow channel 12 can be as small as a monolayer thick when microcontact, aerosol, or inkjet printing is used to deposit a separate material (e.g., spacer layer 20) that attaches the patterned or non-patterned structures or the patterned or non-patterned structure and the lid. As other examples, the depth of the flow channel 12 can be about 1 μm, about 10 μm, about 50 μm, about 100 μm, or more. In an example, the depth may range from about 10 μm to about 100 μm. In another example, the depth may range from about 10 μm to about 30 μm. In still another example, the depth is about 5 μm or less. It is to be understood that the depth of the flow channel 12 may be greater than, less than or between the values specified above.

Each flow channel 12 is in fluid communication with an inlet 14 and an outlet 16. As depicted in FIG. 1, the inlet 14 and outlet 16 of each flow channel 12 are positioned at opposed ends of the flow cell 12. The inlets 14 and outlets 16 of the respective flow channels 12 may be positioned anywhere along the length and width of the flow channel 12 that enables desirable fluid flow.

The inlet 14 allows fluids to be introduced into the flow channel 12, and the outlet 16 allows fluid to be extracted from the flow channel 12. Each of the inlets 14 and outlets 16 is fluidly connected to a fluidic control system (including, e.g., reservoirs, pumps, valves, waste containers, and the like) which controls fluid introduction and expulsion.

FIG. 2A through FIG. 2C, FIG. 3A, and FIG. 3B depict different examples of the architecture within the flow channel 12.

Electrochemically Regenerable Flow Cells

Figure 2B:
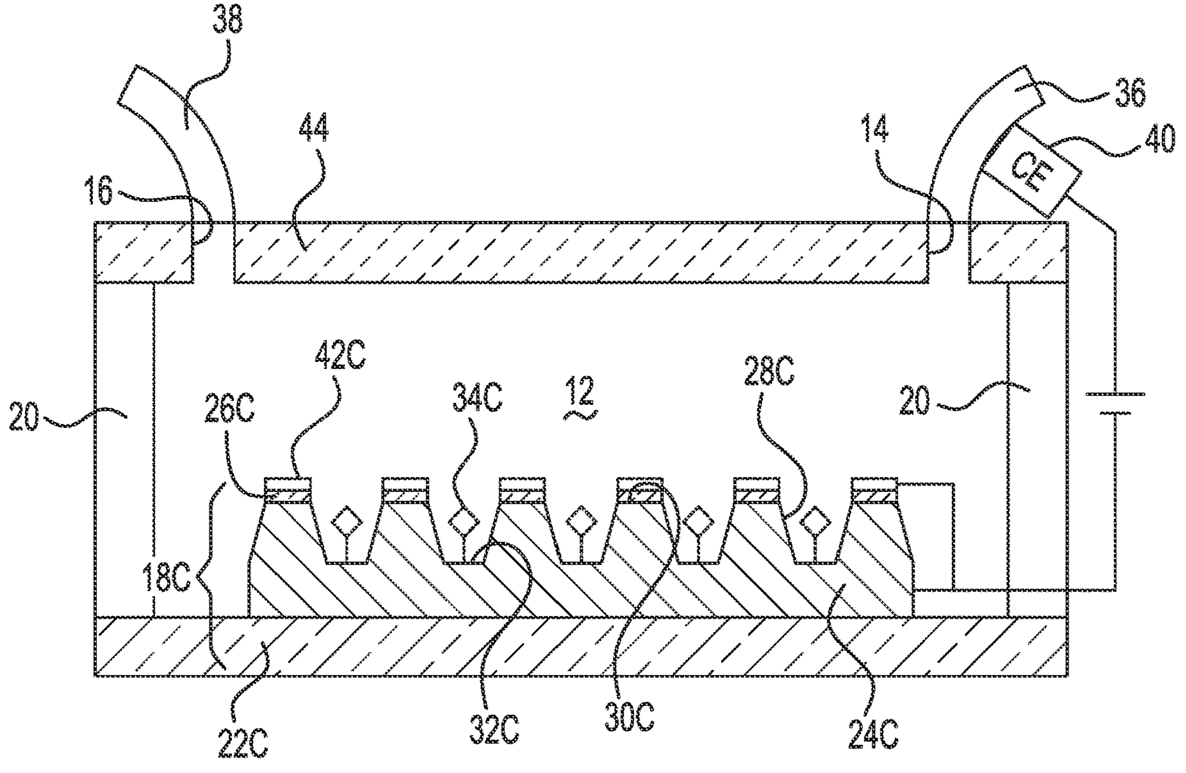
FIG. 2B is a cross-sectional view taken along line 2B-2B in FIG. 1, of another example of a flow cell having an electrochemically regenerable surface.
Figure 2C:
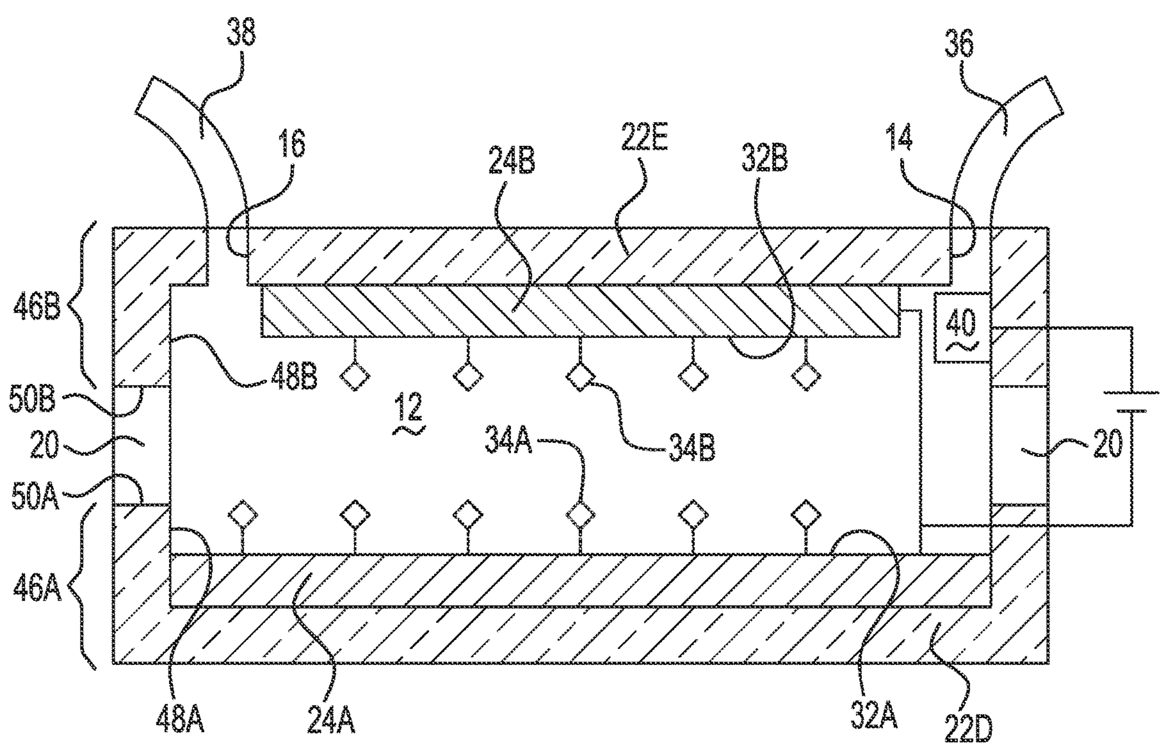
FIG. 2C is a cross-sectional view taken along line 2C-2C in FIG. 1, of yet another example of a flow cell having an electrochemically regenerable surface.

Some of the architecture within the flow channel 12 is designed for electrochemical regeneration of the flow cell surface. Various examples are shown in FIG. 2A through FIG. 2C.

Referring now to FIG. 2A, one example of the architecture within the flow channel 12 includes two patterned structures 18A, 18B that are attached to one another. The flow channel 12 is formed between the two patterned structures 18A, 18B. In another example (not shown), the patterned structure 18A may be attached to a lid (similar to the example shown in FIG. 2B). In this other example, the flow channel 12 is formed between the patterned structure 18A and the lid.

The patterned structures 18A, 18B (or the patterned structure 18A and the lid) may be attached to one another through a spacer layer 20. The spacer layer 20 may be any material that will seal portions of the patterned structures 18A, 18B together or portions of the patterned structure 18A and the lid. As examples, the spacer layer 20 may be an adhesive, a radiation-absorbing material that aids in bonding, or the like. In some examples, the spacer layer 20 is the radiation-absorbing material, e.g., KAPTON® black. The patterned structures 18A, 18B or the patterned structure 18A and the lid may be bonded using any suitable technique, such as laser bonding, diffusion bonding, anodic bonding, eutectic bonding, plasma activation bonding, glass frit bonding, or others methods known in the art.

Each of the patterned structures 18A, 18B includes a substrate 22A, 22B, a working electrode 24A, 24B, and a patterned insulating material 26A, 26B positioned over the working electrode 24A, 24B. The patterned insulating material 26A, 26B defines depressions 28A, 28B separated by interstitial regions 30A, 30B. In this example, the surface 32A, 32B of working electrode 24A, 24B is exposed at each of the depressions 28A, 28B.

In this example, each substrate 22A, 22B is a single layer structure. Each substrate 22A, 22B is electrically insulating and, in some examples, is transparent to excitation and emission wavelength(s) used during nucleic acid analysis. For example, when the patterned structures 18A, 18B are attached to one another, the substrates 22A, 22B are electrically insulating and transparent. Alternatively, when the patterned structure 18A is attached to a lid, the substrate 22A is electrically insulating, but may or may not be transparent because the lid is transparent to the excitation and emission wavelength(s) used during nucleic acid analysis. Examples of electrically insulating and transparent substrate materials include epoxies, siloxanes, glass, modified or functionalized glass, plastics (including acrylics, polystyrene and copolymers of styrene and other materials, polyethylene terephthalate (PET), polycarbonate, cyclic olefin copolymer (COC), some polyamides, silica or silicon oxide ($SiO_2$), fused silica, silica-based materials, silicon nitride ($Si_3N_4$), tantalum pentoxide ($Ta_2O_5$) or other tantalum oxide(s) ($TaO_x$), hafnium oxide ($HfO_2$), inorganic glasses, or the like.

The form of each substrate 22A, 22B may be a wafer, a panel, a rectangular sheet, a die, or any other suitable configuration. In an example, each substrate 22A, 22B may be a circular wafer or panel having a diameter ranging from about 2 mm to about 300 mm. As a more specific example, each substrate 22A, 22B is a wafer having a diameter ranging from about 200 mm to about 300 mm. In another example, each substrate 22A, 22B may be a rectangular sheet or panel having its largest dimension up to about 10 feet (~3 meters). This type of large substrate 22A, 22B may be divided into several smaller substrates for use in the flow cell 10. As a specific example, each substrate 22A, 22B is a rectangular die having a width ranging from about 0.1 mm to about 10 mm. While example dimensions have been provided, it is to be understood that a substrate 22A, 22B with any suitable dimensions may be used.

In FIG. 2A, the inlet 14 and outlet 16 are depicted at opposed sides of the flow channel 12. This positioning is different from that shown in FIG. 1, where the inlet 14 and outlet 16 are at the opposed ends of the flow channel 12. As such, the cross-sectional view in FIG. 2A includes a modification that is not depicted in FIG. 1. As noted herein, the inlet 14 and outlet 16 may be positioned anywhere along the length and width of the flow channel 12 that enables desirable fluid flow.

The illustration of the inlet 14 and outlet 16 in FIG. 2A is included to facilitate understanding of how the inlet 14 and outlet 16 can be formed through one of the substrates 22A, 22B. The inlet 14 and the outlet 16 are respective through-holes that connect the flow channel 12 to inlet fluidics 36 (e.g., tubing, fluid lines, reagent reservoirs, etc.) and outlet fluidics 38 (e.g., tubing, fluid lines, waste containers, etc.). The inlet 14 and outlet 16 may be formed in the same substrate 22A or 22B, or in opposite substrates (e.g., the inlet 14 is formed in the substrate 22A and the outlet 16 is formed in the substrate 22B).

In the architecture of FIG. 2A, the working electrodes 24A, 24B are respectively positioned on the substrates 22A, 22B. Each working electrode 24A, 24B may include any suitable electrode material, such as gold (Au), silver (Ag), silver chloride (AgCl), platinum (Pt), titanium (Ti), molybdenum (Mo), indium tin oxide (ITO), indium zin oxide (IZO), carbon (e.g., graphene, carbon nanotube sheets), conductive polymers (e.g., poly(3,4-ethylenedioxythiophene) (PEDOT), polypyrrole (PPy), polyaniline (PANI)), etc. When the patterned structures 18A, 18B are attached to one another, the working electrodes 24A, 24B should be transparent to excitation and emission wavelength(s) used during nucleic acid analysis. Examples of transparent materials include indium tin oxide (ITO), graphene, conductive polymers, ultrathin metal layers (e.g., thickness of 10 nm or less), etc. When the patterned structure 18A is attached to a lid, the electrode 24A may or may not be transparent because the lid is transparent to excitation and emission wavelength(s) used during nucleic acid analysis.

The electrodes 24A, 24B may have any suitable thickness. As examples, the thickness of each electrode 24A, 24B may be 10 nm or less (e.g., if transparency is desired) or 50 nm or more (e.g., 200 nm, 500 nm, 1 μm, 25 μm, etc.). Thicker electrodes 24A, 24B may be more mechanically robust and exhibit chemical stability. If the regeneration process involves stripping of the electrode surface, the electrodes 24A, 24B each have a thickness of at least 50 μm.

In the example of FIG. 2A, each electrode 24A, 24B is non-patterned, and thus is a continuous layer on the respective substrate 22A, 22B. The electrode 24A, 24B may be deposited on the substrate 12 using a suitable deposition technique (e.g., sputtering), or may be a pre-formed sheet that is attached to the substrate 22A, 22B, e.g., using an adhesive.

In the architecture of FIG. 2A, each patterned insulating material 26A, 26B is positioned over the working electrode 24A, 24B. Each patterned insulating material 26A, 26B defines depressions 28A, 28B, which are separated by interstitial regions 30A, 30B.

It is to be understood that any electrically insulating material that can be selectively deposited, or deposited and patterned to form the depressions 28A, 28B and the interstitial regions 30A, 30B may be used for the patterned insulating material 26A, 26B.

In one example, the patterned insulating material 26A, 26B is an inorganic oxide. The inorganic oxide may be selectively applied to the working electrode 24A, 24B via vapor deposition, aerosol printing, or inkjet printing. Examples of suitable inorganic oxides include tantalum oxide, aluminum oxide, silicon oxide, hafnium oxide, etc.

In another example, the patterned insulating material 26A, 26B is a resin. The resin may be applied to the working electrode 24A, 24B and then patterned. Suitable deposition techniques include chemical vapor deposition, dip coating, dunk coating, spin coating, spray coating, puddle dispensing, ultrasonic spray coating, doctor blade coating, aerosol printing, screen printing, microcontact printing, etc. Suitable patterning techniques include photolithography, nanoimprint lithography (NIL), stamping techniques, embossing techniques, molding techniques, microetching techniques, printing techniques, etc.

Some examples of suitable resins include a polyhedral oligomeric silsesquioxane based resin (e.g., POSS® from Hybrid Plastics), a non-polyhedral oligomeric silsesquioxane epoxy resin, a poly(ethylene glycol) resin, a polyether resin (e.g., ring opened epoxies), an acrylic resin, an acrylate resin, a methacrylate resin, an amorphous fluoropolymer resin (e.g., CYTOP® from Bellex), and combinations thereof.

As used herein, the term "polyhedral oligomeric silsesquioxane" refers to a chemical composition that is a hybrid intermediate (e.g., $RSiO_{1.5}$) between that of silica ($SiO_2$) and silicone ($R_2SiO$). An example of polyhedral oligomeric silsesquioxane may be that described in Kehagias et al., Microelectronic Engineering 86 (2009), pp. 776-778, which is incorporated by reference in its entirety. In an example, the composition is an organosilicon compound with the chemical formula $[RSiO_{3/2}]_n$, where the R groups can be the same or different. Example R groups for polyhedral oligomeric silsesquioxane include epoxy, azide/azido, a thiol, a poly(ethylene glycol), a norbornene, a tetrazine, acrylates, and/or methacrylates, or further, for example, alkyl, aryl, alkoxy, and/or haloalkyl groups. Examples of the polyhedral oligomeric silsesquioxane resin may include one or more different cage or core structures as monomeric units.

As mentioned, the patterned insulating materials 26A, 26B define the depressions 28A, 28B. Many different layouts of the depressions 28A, 28B may be envisaged, including regular, repeating, and non-regular patterns. In an example, the depressions 28A, 28B are disposed in a hexagonal grid for close packing and improved density. Other layouts may include, for example, rectangular layouts, triangular layouts, and so forth. In some examples, the layout or pattern can be an x-y format in rows and columns. In some other examples, the layout or pattern can be a repeating arrangement of the depressions 28A, 28B and the interstitial regions 30A, 30B. In still other examples, the layout or pattern can be a random arrangement of the depressions 28A, 28B and the interstitial regions 30A, 30B.

The layout or pattern may be characterized with respect to the density (number) of the depressions 28A, 28B in a defined area. For example, the depressions 28A, 28B may be present at a density of approximately 2 million per $mm^2$. The density may be tuned to different densities including, for example, a density of about 100 per $mm^2$, about 1,000 per $mm^2$, about 0.1 million per $mm^2$, about 1 million per $mm^2$, about 2 million per $mm^2$, about 5 million per $mm^2$, about 10 million per $mm^2$, about 50 million per $mm^2$, or more, or less. It is to be further understood that the density can be between one of the lower values and one of the upper values selected from the ranges above, or that other densities (outside of the given ranges) may be used. As examples, a high density array may be characterized as having depressions 28A, 28B separated by less than about 100 nm, a medium density array may be characterized as having the depressions 28A, 28B separated by about 400 nm to about 1 μm, and a low density array may be characterized as having the depressions 28A, 28B separated by greater than about 1 μm.

The layout or pattern of the depressions 28A, 28B may also or alternatively be characterized in terms of the average pitch, or the spacing from the center of one depression 28A, 28B to the center of an adjacent depression 28A, 28B (center-to-center spacing) or from the right edge of one depression 28A, 28B to the left edge of an adjacent depression 28A, 28B (edge-to-edge spacing). The pattern can be regular, such that the coefficient of variation around the average pitch is small, or the pattern can be non-regular in which case the coefficient of variation can be relatively large. In either case, the average pitch can be, for example, about 50 nm, about 0.1 μm, about 0.5 μm, about 1 μm, about 5 μm, about 10 μm, about 100 μm, or more or less. The average pitch for a particular pattern can be between one of the lower values and one of the upper values selected from the ranges above. In an example, the depressions 28A, 28B have a pitch (center-to-center spacing) of about 1.5 μm. While example average pitch values have been provided, it is to be understood that other average pitch values may be used.

The size of each depression 28A, 28B may be characterized by its volume, opening area, depth, and/or diameter. For example, the volume can range from about $1\times10^{-3}$ $\mu m^3$ to about 100 $\mu m^3$, e.g., about $1\times10^{-2}$ $\mu m^3$, about 0.1 $\mu m^3$, about 1 $\mu m^3$, about 10 $\mu m^3$, or more, or less. For another example, the opening area can range from about $1\times10^{-3}$ $\mu m^2$ to about 100 $\mu m^2$, e.g., about $1\times10^{-2}$ $\mu m^2$, about 0.1 $\mu m^2$, about 1 $\mu m^2$, at least about 10 $\mu m^2$, or more, or less. For still another example, the depth can range from about 0.1 μm to about 100 μm, e.g., about 0.5 μm, about 1 μm, about 10 μm, or more, or less. For yet another example, the diameter or length and width can range from about 0.1 μm to about 100 μm, e.g., about 0.5 μm, about 1 μm, about 10 μm, or more, or less.

In the architecture of FIG. 2A, the surface 32A, 32B of each working electrode 24A, 24B is exposed at each of the respective depressions 28A, 28B.

In some examples, the exposed working electrode surface 32A, 32B is unmodified. By "unmodified," it is meant that the electrode material is not functionalized or otherwise treated to add non-native surface groups. When the exposed working electrode surface 32A, 32B is unmodified, it is to be understood that the moiety shown in phantom at reference numerals 34A, 34B are not present in the patterned structure 18A, 18B. In these examples, the native functional groups at the working electrode surface 32A, 32B are capable of attaching to a linking moiety of a complex that includes the desired surface chemistry or that can attach to the desired surface chemistry.

In other examples, the exposed working electrode surface 32A, 32B is modified with one member 34A, 34B of a transition metal complex binding pair. A transition metal complex binding pair includes a transition metal complex and another entity (e.g., an additional ligand) that is capable of binding to the transition metal complex. The transition metal complex includes a central atom or ion (which is usually metallic), and a surrounding array of bound molecules or ions (known as ligands).

Transition metal complexes are able to change their coordination sphere, and the number of ligands that can be accommodated changes based on the degree of oxidation. The transition metal complexes used in the example shown in FIG. 2A can be reversibly oxidized and reduced in response to an electric field generated using the working electrodes 24A, 24B. As such, this example of the transition metal complex binding pair may be referred to as an electrochemically responsive transition metal complex binding pair.

In some instances, the transition metal complex is the member 34A, 34B that is bound to the exposed working electrode surface 32A, 32B, and the ligand is introduced as part of the surface chemistry. As one example, the electrochemically responsive transition metal complex binding pair includes a ferrocenyl-poly(propylene imine dendrimer (the transition metal complex) and β-cyclodextrin (the ligand), and the ferrocenyl-poly(propylene imine dendrimer is the member 34A, 34B that is bound to the exposed working electrode surface 32A, 32B. In other instances, the ligand is the member 34A, 34B that is bound to the exposed working electrode surface 32A, 32B, and the transition metal complex is introduced as part of the surface chemistry. As one example, the electrochemically responsive transition metal complex binding pair includes a zinc porphyrin complex (the transition metal complex) and pyridine (the ligand), and the pyridine is the member 34A, 34B that is bound to the exposed working electrode surface 32A, 32B.

The attachment of the member 34A, 34B to the exposed working electrode surface 32A, 32B may involve covalent bonding or non-covalent bonding. As one example, pyridine diazonium or other suitable chemically functionalized pyridines can bond to surface groups of carbon-based electrodes, indium tin oxide electrodes, platinum electrodes, palladium electrodes, or gold electrodes. As another example, ferrocenyl-poly(propylene imine) dendrimers can attach to gold electrodes through thiol, thiolate, amine, bromo, or iodo linkers. The imine of the ferrocenyl-poly(propylene imine) dendrimers may also react with any nucleophilic working electrode surface 32A, 32B. Additionally, ITO working electrodes can be coated with any trimethoxy, triethoxy, or chloro organosilane with a functional group capable of reacting with the member 34A, 34B. One example is aminopropyl trimethoxy silane (APTES), but the amine can be replaced by a carboxylic acid, a thiol, an aldehyde, an acrylate, etc. As yet another example, pyridine may be attached to indium tin oxide electrodes through silane linkers. As a specific example, the working electrode surface 32A, 32B is coated with 2-(trimethoxysilylethyl)pyridine, which includes the first member 34A, 34B and the silane linker. Non-covalent bonding (e.g., biotin-streptavidin) may be used as long as neither member of the non-covalent binding pair can act as a ligand for the transition metal complex being used.

In the architecture of FIG. 2A, the working electrodes 24A, 24B are electrically connected to a counter electrode 40. The counter electrode 40 may be in any position that enables it to be in contact with a fluid (introduced into the flow channel 12) at the same time that the exposed surfaces 32A, 32B of the working electrodes 24A, 24B are in contact with the fluid. The fluid bridges the respective working electrodes 24A, 24B to the counter electrode 40. In the example shown in FIG. 2A, the counter electrode 40 is positioned in fluidic contact with the inlet fluidics 36. For example, the counter electrode 40 is integrated into a fluid line that is operatively connected to the fluid inlet 14. In this example, fluid fills the flow channel 12 and extends into the fluid line containing the counter electrode 40. In other examples, the counter electrode 40 may be positioned on one of the substrates 22A, 22B so that it is physically separate from the respective working electrode 24A, 24B.

In the example shown in FIG. 2A, a single counter electrode 40 is electrically connected to both of the working electrodes 24A, 24B. In this example, a bias may be applied between the counter electrode 40 and one of the working electrodes, e.g., 24A, to attach or detach surface chemistry at the exposed surface(s) 32A, and then a bias may be applied between the counter electrode 40 and the other of the working electrodes, e.g., 24B, to attach or detach surface chemistry at the exposed surface(s) 32B. In other examples, respective counter electrodes may be individually electrically attached to each of the working electrodes 24A, 24B.

It is to be understood that some of the surface chemistry disclosed herein may be attached without the electrical trigger. For example, the surface chemistry that utilizes metal-coordination chemistry or other non-electrically induced reactions will react without an electrical bias, and then the electric bias is used to trigger desorption, degradation, dissociation, etc. (e.g., via oxidation or reduction).

Examples of suitable materials for the counter electrode 40 include platinum, silver, gold, brass, conductive carbon materials (e.g., graphite), copper, titanium, palladium, ruthenium, silver/silver chloride, conductive organic materials, etc.

The working electrodes 24A, 24B and the counter electrode 40 are electrically connected to a controller (not shown), which is operable to selectively apply the desired electrical bias. The controller may include a potentiostat (for reading current and voltage levels).

Some examples of the patterned structures 18A, 18B shown in FIG. 2A include a second working electrode 42A, 42B. The second working electrodes 42A, 42B are respectively positioned over the patterned insulating materials 26A, 26B and thus are physically isolated from the working electrodes 24A, 24B.

The second working electrodes 42A, 42B may be any of the materials set forth herein for the working electrodes 24A, 24B. The second working electrodes 42A, 42B are applied to the respective interstitial regions 30A, 30B and not to the exposed surfaces 32A, 32B. The second working electrodes 42A, 42B may be deposited using a selective deposition process or they may be pre-formed patterned sheets that are attached to the respective interstitial regions 30A, 30B, e.g., using an adhesive.

In the example shown in FIG. 2A, the counter electrode 40 is also electrically connected to both of the second working electrodes 42A, 42B. In this example, respective biases may simultaneously be applied between the counter electrode 40 and one of the working electrodes, e.g., 24A, and between the counter electrode 40 and a corresponding one of the second working electrodes, e.g., 42A. For example, an adsorption bias applied to working electrode, e.g., 24A, initiates attachment of the surface chemistry at the exposed surface(s) 32A, while an opposite bias (a desorption bias) simultaneously applied to the second working electrodes 42A repels the surface chemistry in order to keep the interstitials 30A clean. Similarly, respective biases may simultaneously be applied between the counter electrode 40 and the other of the working electrodes, e.g., 24B, and between the counter electrode 40 and a corresponding one of the second working electrodes, e.g., 42B. The adsorption bias applied to working electrode, e.g., 24B initiates attachment of the surface chemistry at the exposed surface(s) 32B, while the opposite bias (a desorption bias) simultaneously applied to the second working electrode 42B repels the surface chemistry in order to keep the interstitials 30B clean. Application of the desorption voltage bias to the second working electrodes 42A, 42B during the functionalization of the working electrodes 24A, 24B with the surface chemistry helps to ensure that the interstitial regions 30A, 30B remain free of the surface chemistry. The same or a similar desorption bias may also be applied to the working electrodes 24A, 24B and to the second working electrodes 42A, 42B during detachment or desorption of the surface chemistry from the electrode surfaces 32A, 32B.

As such, in some of the examples of FIG. 2A, the flow cell includes: the substrate 22A, 22B; the first working electrode 24A, 24B positioned over the substrate 22A, 22B; the patterned insulating material 26A, 26B positioned over the first working electrode 24A, 24B, the patterned insulating material 26A, 26B defining depressions 28A, 28B separated by interstitial regions 30A, 30B, wherein a surface 32A, 32B of the first working electrode 24A, 24B is exposed at each of the depressions 28A, 28B, the surface 32A, 32B being unmodified or modified with a first member 34A, 34B of a transition metal complex binding pair; the second working electrode 42A, 42B positioned over the interstitial regions 30A, 30B; a counter electrode 40 electrically connected to each of the first working electrode 24A, 24B and the second working electrode 42A, 42B; a flow channel 12 in fluid communication with the surface 32A, 32B of the first working electrode 24A, 24B and with the second working electrode 42A, 42B; and a controller electrically connected to the first working electrode 24A, 24B, the second working electrode 42A, 42B, and the counter electrode 40.

Referring now to FIG. 2B, another example of the architecture within the flow channel 12 includes one patterned structure 18C that is attached to a lid 44. In this example, the flow channel 12 is formed between the patterned structure 18C and the lid 44. In another example (not shown), two patterned structures 18C may be attached to one another (similar to the example shown in FIG. 2A). In this other example, the flow channel 12 is formed between two of the patterned structures 18C.

The lid 44 may be any material that is transparent to an excitation light that is directed toward the patterned structure 18C. As examples, the lid 44 may be glass (e.g., borosilicate, fused silica, etc.), plastic, or the like. A commercially available example of a suitable borosilicate glass is D 263®, available from Schott North America, Inc. Commercially available examples of suitable plastic materials, namely cyclo olefin polymers, are the ZEONOR® products available from Zeon Chemicals L.P.

The lid 44 may be attached to the patterned structure 18C through the spacer layer 20. The spacer layer 20 may be any of the materials set forth herein. The patterned structure 18C and the lid may be bonded using any suitable technique, such as laser bonding, diffusion bonding, anodic bonding, eutectic bonding, plasma activation bonding, glass frit bonding, or others methods known in the art. In this example, the transparent lid 44 is connected to the substrate 22D and forms a surface of the flow channel 12.

In the architecture shown in FIG. 2B, the patterned structure 18C includes a substrate 22C, a working electrode 24C that is patterned over the substrate 22C to define depressions 28C separated by interstitial regions 30C, where the surface 32C of working electrode 24C is exposed at each of the depressions 28C, and a patterned insulating material 26C positioned over the interstitial regions 30C.

In this example, the substrate 22C is a single layer structure. The substrate 22C is electrically insulating and, may or may not be transparent because the lid 44 is transparent. Any of the examples set forth herein for the substrates 22A, 22B may be used for the substrate 22C. Other suitable examples for the substrate 22C include polypropylene, polyurethanes, cyclic olefins/cyclo-olefin polymers (COP) (such as ZEONOR® from Zeon), polyimides, etc.), ceramics/ceramic oxides, aluminum silicate, silicon, and silicon nitride ($Si_3N_4$). When two patterned structures 18C are attached to one another, the substrates 22C are electrically insulating and transparent. The form of the substrate 22C may be any of the examples disclosed herein.

In FIG. 2B, the inlet 14 and outlet 16 are depicted at opposed sides of the flow channel 12. This positioning is different from that shown in FIG. 1, where the inlet 14 and outlet 16 are at the opposed ends of the flow channel 12. As such, the cross-sectional view in FIG. 2B includes a modification that is not depicted in FIG. 1. As noted herein, the inlet 14 and outlet 16 may be positioned anywhere along the length and width of the flow channel 12 that enables desirable fluid flow.

The illustration of the inlet 14 and outlet 16 in FIG. 2B is included to facilitate understanding of how the inlet 14 and outlet 16 can be formed through the lid 44. The inlet 14 and the outlet 16 are respective through-holes that connect the flow channel 12 to inlet fluidics 36 (e.g., tubing, fluid lines, reagent reservoirs, etc.) and outlet fluidics 38 (e.g., tubing, fluid lines, waste containers, etc.). The inlet 14 and outlet 16 may both be formed in the lid 44 or the substrate 22C, or one (e.g., the inlet 14) may be formed in the lid 44 and the other (e.g., the outlet 16) may be formed in the substrate 22C.

In the architecture of FIG. 2B, the working electrode 24C is positioned on the substrate 22C. The working electrode 24C may be any of the electrode materials set forth herein for the electrodes 24A, 24B. When the patterned structure 18C is attached to the lid 44, the working electrode 24C may or may not be transparent. When the patterned structure 18C is attached to another patterned structure 18C, the working electrode 24C should be any of the transparent electrode materials set forth herein. The electrode 24C may also have any suitable thickness.

In the example of FIG. 2B, the working electrode 24C is patterned to define depressions 28C separated by interstitial regions 30C. The patterned working electrode 24C may be a pre-formed grid that is attached to the substrate 22C, e.g., using an adhesive, or may be deposited on the substrate 22C in a desirable pattern using a suitable technique. As one example, an additive technique for generating the patterned working electrode 24C may involve photolithography and sputtering of the desired electrode material. As another example, a subtractive technique for generating the patterned working electrode 24C may involve blanket deposition of the desired electrode material followed by photolithography and etching. The pattern may include thicker portions to form the interstitial regions 30C and thinner portions to form the depressions 28C between the interstitial regions 30C. Any of the patterns, layouts, and dimensions set forth herein for the depressions 28A, 28B in FIG. 2A may be used for the depressions 28C shown in FIG. 2B.

In the architecture of FIG. 2B, the patterned insulating material 26C is positioned over the interstitial regions 30C of the working electrode 24C. It is to be understood that any electrically insulating material that can be selectively deposited, or deposited and patterned on the interstitial regions 30C (without depositing on the surfaces 32C in the depressions 28C) may be used for the patterned insulating material 26C. Any of the materials for patterned insulating material 26A, 26B may be used for the patterned insulating material 26C.

In the architecture of FIG. 2B, the surface 32C of the patterned working electrode 24C is exposed at each of the depressions 28C. In some examples, the exposed working electrode surface 32C is unmodified as described herein. In other examples, the exposed working electrode surface 32C is modified with one member 34C (shown in phantom) of the transition metal complex binding pair as described herein.

In the architecture of FIG. 2B, the patterned working electrode 24C is electrically connected to a counter electrode 40. As mentioned herein, examples of suitable materials for the counter electrode 40 include platinum, silver, and gold. The counter electrode 40 may be in any position that enables it to be in contact with a fluid (introduced into the flow channel 12) at the same time that the exposed surfaces 32C of the patterned working electrode 24C are in contact with the fluid. The fluid bridges the patterned working electrode 24C to the counter electrode 40. In the example shown in FIG. 2B, the counter electrode 40 is positioned in fluidic contact with the inlet fluidics 36. In this example, a transparent counter electrode 40 could alternatively be patterned directly onto the lid 44.

The bias applied between the counter electrode 40 and the patterned working electrode 24C attaches or detaches surface chemistry at the exposed surface(s) 32C.

When the flow cell 10 includes two opposed patterned structures 18C (similar to the example shown in FIG. 2A), it is to be understood that a single counter electrode 40 may be electrically connected to the patterned working electrodes 24C of the respective patterned structures 18C. Sequential biases may be applied in order to attach or detach surface chemistry at the exposed surface(s) 32C of the respective patterned structures 18C.

The working electrode 24C and the counter electrode 40 are electrically connected to a controller (not shown), which is operable to selectively apply the desired electrical bias. In this example, the controller may include a potentiostat.

Some examples of the patterned structures 18C shown in FIG. 2B include a second working electrode 42C. The second working electrode 42C is positioned over the patterned insulating material 26C and thus is physically isolated from the patterned working electrode 24C.

The second working electrode 42C may be any of the materials set forth herein for the working electrodes 24A, 24B and the patterned working electrode 24C. The second working electrode 42C is applied to the patterned insulating material 26C and not to the exposed surfaces 32C. The second working electrode 42C may be deposited using a selective deposition process or may be a pre-formed patterned sheet that is attached to the patterned insulating material 26C, e.g., using an adhesive.

In the example shown in FIG. 2B, the counter electrode 40 is also electrically connected to the second working electrode 42C. In this example, respective biases may simultaneously be applied between the counter electrode 40 and the patterned working electrode, e.g., 24C, and between the counter electrode 40 and the second working electrodes, e.g., 42C. For example, an adsorption bias applied to patterned working electrode, e.g., 24C, initiates attachment of the surface chemistry at the exposed surface(s) 32C, while an opposite bias (a desorption bias) simultaneously applied to the second working electrode 42C repels the surface chemistry in order to keep the interstitials 30C clean. The same or a similar desorption bias may also be applied to the working electrode 24C and to the second working electrode 42C during detachment or desorption of the surface chemistry from the electrode surfaces 32C.

As such, in some of the examples of FIG. 2B, the flow cell 10 includes: the substrate 22C; a first patterned working electrode 24C positioned over the substrate 22C, the first patterned working electrode 24C defining depressions 28C separated by interstitial regions 30C, wherein a surface 32C of the first patterned working electrode 24C is exposed at each of the depressions 28C, the surface 32C being unmodified or modified with a first member 34C of a transition metal complex binding pair; a patterned insulating material 26C positioned over the interstitial regions 30C; a second patterned working electrode 42C positioned over the patterned insulating material 26C; a counter electrode 40 electrically connected to each of the first patterned working electrode 24C and the second patterned working electrode 42C; a flow channel 12 in fluid communication with the surface 32C of the first patterned working electrode 24C and the second patterned working electrode 42C; and a controller electrically connected to the first patterned working electrode 24C, the second patterned working electrode 42C, and the counter electrode 40.

Referring now to FIG. 2C, one example of the architecture within the flow channel 12 includes two non-patterned structures 46A, 46B that are attached to one another. The flow channel 12 is formed between the two non-patterned structures 46A, 46B. In another example (not shown), the non-patterned structure 46A may be attached to a lid 44. In this other example, the flow channel 12 is formed between the non-patterned structure 46A and the lid 44.

Each of the non-patterned structures 46A, 46B includes a substrate 22D, 22E and a working electrode 24A, 24B positioned over a portion of the substrate 22D, 22E. In this example, the entire surface 32A, 32B of each working electrode 24A, 24B is exposed. The non-patterned structures 46A, 46B do not include depressions separated by interstitial regions.

The substrates 22D, 22E are single layer structures. Each substrate 22D, 22E is electrically insulating and, in some examples, is transparent to excitation and emission wavelength(s) used during nucleic acid analysis. For example, when the non-patterned structures 46A, 46B are attached to one another, the substrates 22D, 22E are electrically insulating and transparent. Alternatively, when the non-patterned structure 46A is attached to a lid 44, the substrate 22D is electrically insulating, but may or may not be transparent because the lid 44 is transparent. Any examples of the substrate 22A, 22B may be used for the substrate 22D, 22E. The form of each substrate 22D, 22E may be a wafer, a panel, a rectangular sheet, a die, or any other configuration set forth herein.

In the example shown in FIG. 2C, the substrates 22D, 22E have a concave region 48A, 48B surrounded by edge regions 50A, 50B. The concave region 48A, 48B provides a designated area where the working electrodes 24A, 24B can be attached. The edge regions 50A, 50B provide bonding regions where the two non-patterned structures 46A, 46B can be attached to one another or where one non-patterned structure 46A can be attached to a lid 44.

The non-patterned structures 46A, 46B (or the non-patterned structure 46A and the lid 44) may be attached to one another through the spacer layer 20 at the edge regions 50A, 50B. The spacer layer 20 may be any of the materials set forth herein. The non-patterned structures 46A, 46B may be bonded using any suitable technique, such as laser bonding, diffusion bonding, anodic bonding, eutectic bonding, plasma activation bonding, glass frit bonding, or others methods known in the art.

In the architecture of FIG. 2C, the working electrodes 24A, 24B are respectively positioned in the concave regions 48A, 48B of the substrates 22D, 22E. The working electrodes 24A, 24B are non-patterned electrodes that extend across the bottom surface of the concave region 48A, 48B. The working electrodes 24A, 24B may be any of the examples set forth herein.

The electrode 24A, 24B may be deposited in the concave regions 48A, 48B of the substrates 22D, 22E using a suitable deposition technique (e.g., sputtering), or may be a preformed sheet that is attached to the concave regions 48A, 48B, e.g., using an adhesive.

In FIG. 2C, the inlet 14 and outlet 16 are depicted at opposed sides of the flow channel 12. This positioning is different from that shown in FIG. 1, where the inlet 14 and outlet 16 are at the opposed ends of the flow channel 12. As such, the cross-sectional view in FIG. 2C includes a modification that is not depicted in FIG. 1. As noted herein, the inlet 14 and outlet 16 may be positioned anywhere along the length and width of the flow channel 12 that enables desirable fluid flow.

The illustration of the inlet 14 and outlet 16 in FIG. 2C is included to facilitate understanding of how the inlet 14 and outlet 16 can be formed through one of the substrates 22D, 22E. The inlet 14 and the outlet 16 are respective through-holes that connect the flow channel 12 to inlet fluidics 36 (e.g., tubing, fluid lines, reagent reservoirs, etc.) and outlet fluidics 38 (e.g., tubing, fluid lines, waste containers, etc.). The inlet 14 and outlet 16 may be formed in the same substrate 22D or 22E, or in opposite substrates (e.g., the inlet in substrate 22D and the outlet in substrate 22E).

In the architecture of FIG. 2C, the surface 32A, 32B of each working electrode 24A, 24B is exposed across the flow channel 12. In some examples, the exposed working electrode surface 32A, 32B is unmodified as described herein. In other examples, the exposed working electrode surface 32A, 32B is modified with one member 34A, 34B of the transition metal complex binding pair as described herein.

In the architecture of FIG. 2C, the working electrodes 24A, 24B are electrically connected to a counter electrode 40. The counter electrode 40 may be in any position that enables it to be in contact with a fluid that is introduced into the flow channel 12 at the same that that the working electrodes 24A, 24B are in contact with the fluid. The fluid bridges the respective working electrodes 24A, 24B to the counter electrode 40. In the example shown in FIG. 2C, the counter electrode 40 is positioned within the flow channel 12 along a sidewall of the concave region 48B.

In the example shown in FIG. 2C, a single counter electrode 40 is electrically connected to both of the working electrodes 24A, 24B. In this example, a bias may be applied between the counter electrode 40 and one of the working electrodes, e.g., 24A, to attach or detach surface chemistry at the exposed surface(s) 32A, and then a bias may be applied between the counter electrode 40 and the other of the working electrodes, e.g., 24B, to attach or detach surface chemistry at the exposed surface(s) 32B. In other examples, respective counter electrodes may be individually electrically attached to each of the working electrodes 24A, 24B.

Examples of suitable materials for the counter electrode 40 include platinum, silver, and gold.

The working electrodes 24A, 24B and the counter electrode 40 are electrically connected to a controller (not shown), which is operable to selectively apply the desired electrical bias. The controller may include a potentiostat.

In any of the example shown in FIG. 2A through FIG. 2C, the second patterned structure 18B, the lid 44, or the second non-patterned structure 46B may be replaced with a transparent counter electrode 40. In this example, the counter electrode 40 is a transparent counter electrode that forms a surface of the flow channel 12.

Visible Light Regenerable Flow Cells

Figure 3A:
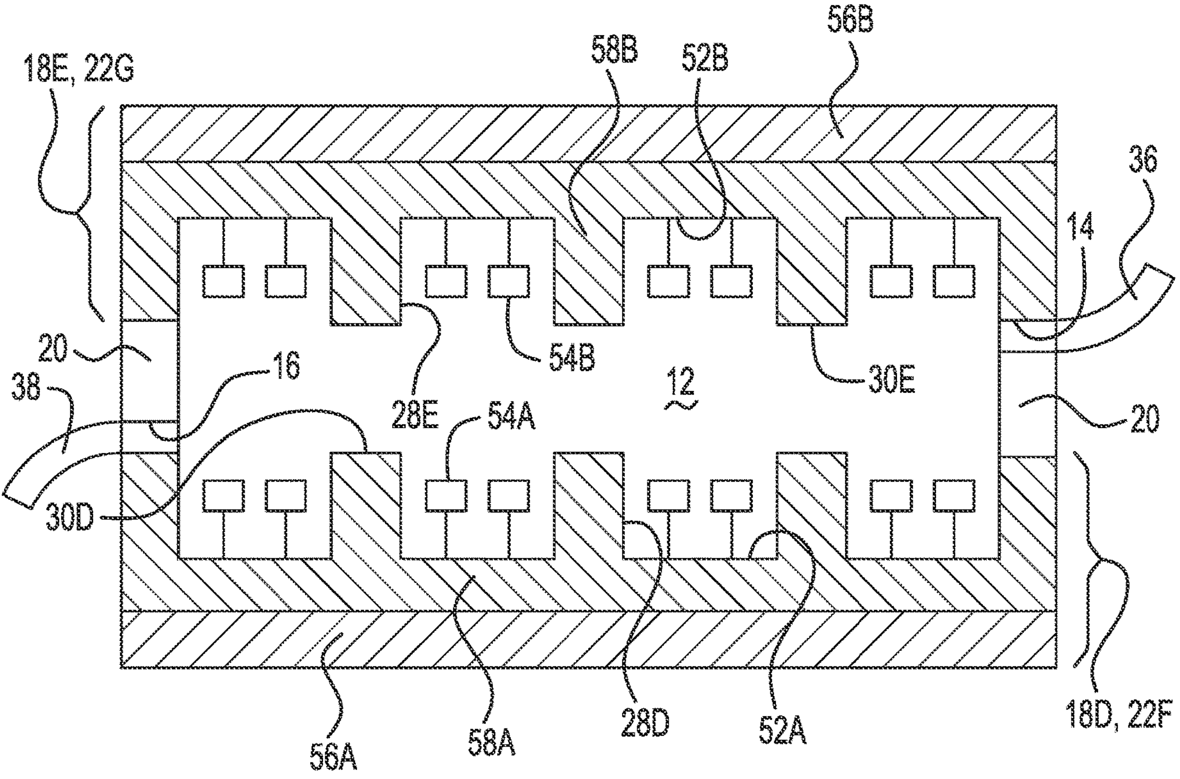
FIG. 3A is a cross-sectional view taken along line 3A-3A in FIG. 1, of an example of a flow cell having a visible light regenerable surface.

Some of the architecture within the flow channel 12 is designed for visible light regeneration of the flow cell surface. Two examples are shown in FIG. 3A and FIG. 3B. In these examples, the flow cell 10 includes a flow channel 12 and a substrate 22F, 22G, 22H, 22I having a surface 52A, 52B, 52C, 52D that is at least partially exposed to the flow channel 12, the surface 52A, 52B, 52C, 52D being modified with a visible light responsive first member 54A, 54B of a transition metal complex binding pair.

Referring now to FIG. 3A, another example of the architecture within the flow channel 12 includes two patterned structures 18D, 18E that are attached to one another. The flow channel 12 is formed between the two patterned structures 18D, 18E. In another example (not shown), the patterned structure 18D may be attached to a lid 44. In this other example, the flow channel 12 is formed between the patterned structure 18D and the lid 44.

The two patterned structures 18D, 18E are attached through the spacer layer 20. The spacer layer 20 may be any of the materials set forth herein. The patterned structures 18D, 18E may be bonded using any suitable technique, such as laser bonding, diffusion bonding, anodic bonding, eutectic bonding, plasma activation bonding, glass frit bonding, or others methods known in the art.

The substrate 22F, 22G of the patterned structures 18D, 18E is a multi-layered structure. The multi-layered structure includes a base support 56A, 56B and a patterned layer 58A, 58B over the base support 56A, 56B. When the patterned structures 18D, 18E are adhered together, the components of the multi-layered structures should be transparent to visible light (used for absorption and/or desorption of the surface chemistry and for nucleic acid analysis) or transparent to both transparent to visible light (used for absorption and/or desorption of the surface chemistry) and ultraviolet light (used for nucleic acid analysis). When the patterned structure 18D is adhered to a lid 44, the components of the multi-layered structure may or may not be transparent because the lid 44 is transparent to both visible light and ultraviolet light.

Examples of the base support 56A, 56B of the substrate 22F, 22G include glass, UV fused silica, $CaF_2$, $MgF_2$, $BaF_2$, quartz, sapphire, and some ceramics. Other suitable materials for the base support 56A, 56B include rigid transparent plastics, such as polyethylene terephthalate, cyclic olefin copolymer (COC), and polycarbonate. Examples of the patterned layer 58A, 58B of the substrate 22F, 22G include polyhedral oligomeric silsesquioxane based resins, acrylate, methacrylate, thiol, or epoxy functional resins that are photocurable in presence of a photoinitiator and/or photoacid generator, UV/VIS transparent ceramic oxides (e.g., tantalum pentoxide), indium tin oxide (suitable, e.g., for a Red/Green system), and any material that can be selectively deposited, or deposited and patterned to form depressions 28D, 28E and interstitial regions 30D, 30E. An example of the multi-layered structure (substrate 22F, 22G) includes glass as the base support 56A, 56B, with a layer of tantalum oxide (e.g., tantalum pentoxide or another tantalum oxide(s) ($TaO_x$)) or another UV/VIS transparent ceramic oxide as the patterned layer 58A, 58B.

The form of each substrate 22F, 22G may be a wafer, a panel, a rectangular sheet, a die, or any other suitable configuration disclosed herein.

In the example of FIG. 3A, the patterned layer 58A, 58B is patterned to define depressions 28D, 28E separated by interstitial regions 30D, 30E. Any of the patterns, layouts, and dimensions set forth herein for the depressions 28A, 28B in FIG. 2A may be used for the depressions 28D, 28E shown in FIG. 3A.

In the architecture of FIG. 3A, the patterned layer 58A, 58B of the substrate 22F, 22G is exposed to the flow channel 12. The surfaces 52A, 52B within the depressions 28D, 28E and the interstitial regions 30D, 30E are exposed to the flow channel 12.

In this example, the surfaces 52A, 52B are modified with a visible light responsive first member 54A, 54B of a transition metal complex binding pair. As mentioned herein, transition metal complex binding pair includes a transition metal complex and an additional entity (e.g., a ligand) that is capable of binding to the transition metal complex. In the example shown in FIG. 3A, the transition metal complex is the visible light responsive first member 54A, 54B that is attached to the surfaces 52A, 52B, and the additional ligand is the surface chemistry that is introduced into the flow cell 10. The additional ligand is a visible light responsive second member of the transition metal complex binding pair, which can attach to the visible light responsive first member 54A, 54B and can be cleaved from the visible light responsive first member 54A, 54B upon exposure to visible light.

An example of this transition metal complex binding pair includes a ruthenium complex as the visible light responsive first member 54A, 54B and a functionalized thioether ligand as the visible light responsive second member. The ruthenium complex has the general formula $[Ru(bpy)_2L_2]^{2+}H_2O$, where bpy is 2,2'-bipyridine and L is 4-aminopyridine. The transition metal of the transition metal complex binding pair may alternatively be osmium, iron, cobalt, nickel, rhodium, palladium, iridium, etc. The ligand of the transition metal complex binding pair may alternatively be phenanthrolines, quinoline, imidazole, indoles, and a variety of other heterocycles.

The attachment of the visible light responsive first member 54A, 54B to the surface 52A, 52B may involve covalent bonding or non-covalent bonding. As one example, visible light responsive first member 54A, 54B may be attached to the surface 52A, 52B through a silane linker (e.g., (3-Aminopropyl)trimethoxysilane (APTMS), (3-Aminopropyl)triethoxysilane (APTES), norbornene silane, etc.). In this example, the patterned layer 58A, 58B may be exposed to plasma ashing (to generate —OH groups), silanization, and then polishing to remove the silane linker from the interstitial regions 30D, 30E while leaving the silane linker attached to the surface 52A, 52B. Non-covalent bonding (e.g., biotin-streptavidin) may be used as long as neither member of the non-covalent binding pair can act as a ligand for the transition metal complex being used.

In FIG. 3A, the inlet 14 and outlet 16 are depicted at opposed sides of the flow channel 12. This positioning is different from that shown in FIG. 1, where the inlet 14 and outlet 16 are at the opposed ends of the flow channel 12. As such, the cross-sectional view in FIG. 3A includes a modification that is not depicted in FIG. 1. As noted herein, the inlet 14 and outlet 16 may be positioned anywhere along the length and width of the flow channel 12 that enables desirable fluid flow.

The illustration of the inlet 14 and outlet 16 in FIG. 3A is included to facilitate understanding of how the inlet 14 and outlet 16 can be formed through one of the patterned structures 18D, 18E. The inlet 14 and the outlet 16 are respective through-holes that connect the flow channel 12 to inlet fluidics 36 (e.g., tubing, fluid lines, reagent reservoirs, etc.) and outlet fluidics 38 (e.g., tubing, fluid lines, waste containers, etc.). The inlet 14 and outlet 16 may be formed in the same substrate 22F or 22G, or in opposite substrates as shown in FIG. 3A (e.g., the inlet in substrate 22G and the outlet in substrate 22F).

Referring now to FIG. 3B, another example of the architecture within the flow channel 12 includes two non-patterned structures 46C, 46D that are attached to one another. The flow channel 12 is formed between the two non-patterned structures 46C, 46D. In another example (not shown), the non-patterned structure 46C may be attached to a lid 44. In this other example, the flow channel 12 is formed between the non-patterned structure 46C and the lid 44.

Each of the non-patterned structures 46C, 46D includes a substrate 22H, 22I and the visible light responsive first member 54A, 54B attached to a portion of the surface 52C, 52D of the substrate 22H, 22I. The non-patterned structures 46C, 46D do not include depressions separated by interstitial regions.

In the example shown, the substrates 22H, 22I are single layer structures. Any example of the base support 58A, 58B disclosed herein may be used for the substrate 22H, 22I. The form of each substrate 22H, 22I may be a wafer, a panel, a rectangular sheet, a die, or any other configuration set forth herein.

In the example shown in FIG. 3B, the substrates 22H, 22I have a concave region 48C, 48D surrounded by edge regions 50C, 50D. The concave region 48C, 48D provide a designated area where the visible light responsive first member 54A, 54B can be attached. The edge regions 50C, 50D provide bonding regions where the two non-patterned structures 46C, 46D can be attached to one another or where one non-patterned structure 46C can be attached to a lid 44.

The non-patterned structures 46C, 46D (or the non-patterned structure 46C and the lid 44) may be attached to one another through the spacer layer 20 at the edge regions 50C, 50D. The spacer layer 20 may be any of the materials set forth herein. The non-patterned structures 46C, 46D may be bonded using any suitable technique, such as laser bonding, diffusion bonding, anodic bonding, eutectic bonding, plasma activation bonding, glass frit bonding, or others methods known in the art.

In the architecture of FIG. 3B, the concave region 48C, 48D of the substrate 22H, 22I is exposed to the flow channel 12. The surface 52C, 52D within the concave region 48C, 48D is exposed to the flow channel 12.

In this example, the surfaces 52C, 52D are modified with the visible light responsive first member 54A, 54B of a transition metal complex binding pair. Any example of the visible light responsive first member 54A, 54B and any attachment mechanism to the surfaces 52C, 52D may be used.

In FIG. 3B, the inlet 14 and outlet 16 are depicted at opposed sides of the flow channel 12. This positioning is different from that shown in FIG. 1, where the inlet 14 and outlet 16 are at the opposed ends of the flow channel 12. As such, the cross-sectional view in FIG. 3B includes a modification that is not depicted in FIG. 1. As noted herein, the inlet 14 and outlet 16 may be positioned anywhere along the length and width of the flow channel 12 that enables desirable fluid flow.

The illustration of the inlet 14 and outlet 16 in FIG. 3B is included to facilitate understanding of how the inlet 14 and outlet 16 can be formed through one of the non-patterned structures 46C, 46D. The inlet 14 and the outlet 16 are respective through-holes that connect the flow channel 12 to inlet fluidics 36 (e.g., tubing, fluid lines, reagent reservoirs, etc.) and outlet fluidics 38 (e.g., tubing, fluid lines, waste containers, etc.). The inlet 14 and outlet 16 may be formed in the same substrate 22H, 22I, or in opposite substrates as shown in FIG. 3B (e.g., the inlet in substrate 22I and the outlet in substrate 22H).

Surface Chemistry Complexes

The flow cell 50 disclosed herein is able to receive and attach surface chemistry that temporarily functionalizes the surfaces 32A, 32B, 32C, 52A, 52B for nucleic acid sequencing. The surface chemistry is removable electrochemically or via exposure to visible light. Examples of the surface chemistry will now be described.

Each example of the surface chemistry includes a complex. Each example of the complex includes a linking moiety that is capable of attaching to one or more of the working electrode surfaces 32A, 32B, 32C, 52A, 52B. In some instances, the complex functions as a linker for other surface chemistry that can participate in the nucleic acid analysis. In other instances, the complex includes additional surface chemistry that can participate in the nucleic acid analysis. Examples of different complexes are shown schematically in FIG. 4A through FIG. 4E.

One example complex 60A is shown in FIG. 4A. This complex 60A is electrochemically removable and can be used with the working electrode surfaces 32A, 32B, 32C that are unmodified. The complex 60A includes a linking moiety 62A that is capable of attaching to and detaching from the unmodified working electrode surfaces 32A, 32B, 32C, and an orthogonal functional group 64 that does not attach to the unmodified working electrode surfaces 32A, 32B, 32C.

Because the linking moiety 62A is capable of attaching to and detaching from the unmodified working electrode surface 32A, 32B, 32C, the linking moiety 62A will depend upon electrode material and the native functional groups of the electrode material. When the working electrode 24A, 24B, 24C is selected from the group consisting of carbon-based electrodes, indium tin oxide, platinum, palladium, and gold, the linking moiety 62A is selected from the group consisting of a thiol, a diazonium, an alkyne, a carbene, an adenosine oligonucleotide, a dithioester, an isonitrile, an isothiocyanate, a carboxyl, an amine, a nitrile, a nitro, and a trialkylsilyl. These linking moieties 62A can bond to the native functional groups of the unmodified working electrode surface 32A, 32B, 32C when exposed to suitable reaction conditions and can desorb from the unmodified working electrode surface 32A, 32B, 32C when exposed to a desorption bias. The reaction conditions will depend upon the linking moiety 62A and working electrode 24A, 24B, 24C, and in some instances, the reaction will be spontaneous in the fluid used to introduce the linking moiety 62A. In some examples, these linking moieties 62A can bond to the native functional groups of the unmodified working electrode surface 32A, 32B, 32C i) in the absence of a first bias or ii) when exposed to a first bias and can desorb from the unmodified working electrode surface 32A, 32B, 32C i) when exposed to a bias or ii) when exposed to a second bias that is opposite the first bias. The bias applied for attachment or detachment may range from 0 V to +/−3 V (0 being the absence of the bias), and will depend upon the linking moiety 62A that is used. As one example, a negative bias may be applied to attach a diazonium group (as the linking moiety 62A) to a working electrode surface 32A, 32B, 32C, and a positive bias or a more negative bias may be used for detachment. As other examples, the linking moiety 62A may spontaneously react with the electrode surface 32A, 32B, 32C with no bias (0 V applied), and may be detached at either a positive bias or a negative bias.

The orthogonal functional group 64 is selected so that its reactivity is orthogonal to the linking moiety 62A, and thus is not reactive with the native functional groups of the unmodified working electrode surface 32A, 32B, 32C. The orthogonal functional group 64 is also selected so that it is reactive with a reactive functional group of additional surface chemistry that is to be added to the unmodified working electrode surface 32A, 32B, 32C. The additional surface chemistry that the orthogonal functional group 64 attaches may be primer functionalized hydrogels or particles or pre-clustered hydrogels or particles. As examples, the orthogonal functional group 64 may be an azide, which covalently attaches to an alkyne (e.g., a dialkyne, strained alkynes) or a tetrazine of the additional surface chemistry; or the orthogonal functional group 64 is an epoxy, which covalently attaches to a free amine group of the additional surface chemistry; or the orthogonal functional group 64 is an activated carboxylate (e.g., N-hydroxysuccinimide ester), which covalently attaches to a free amine group of the additional surface chemistry; or the orthogonal functional group 64 is an aldehyde which covalently attaches to a hydrazine of the additional surface chemistry; or the orthogonal functional group 64 is a phosphoramidite which covalently attaches to a thioether of the additional surface chemistry; or the orthogonal functional group 64 is an alkylating reagent which covalently attaches to a thioether of the additional surface chemistry. The orthogonal functional group 64 may also be capable of forming a non-covalent bond with the reactive functional group of additional surface chemistry. For example, the orthogonal functional group 64 is biotin which non-covalently bonds to streptavidin of the additional surface chemistry; or the orthogonal functional group 64 is a spy-catcher which non-covalently bonds to a spy-tag of the additional surface chemistry.

Another example complex 60B is shown in FIG. 4B. This complex 60B is electrochemically removable and can be used with the working electrode surfaces 32A, 32B, 32C that are unmodified. The complex 60B includes the linking moiety 62A that is capable of attaching to and detaching from the unmodified working electrode surfaces 32A, 32B, 32C, and a capture oligonucleotide 66.

Any example of the linking moiety 62A may be used in the complex 60B.

The capture oligonucleotide 66 is single stranded nucleic acid sequence that can hybridize to a complementary oligonucleotide of additional surface chemistry that is to be added to the unmodified working electrode surface 32A, 32B, 32C. The capture oligonucleotide 66 may have a length ranging from about 10 nucleotides to about 100 nucleotides, or from about 12 nucleotides to about 60 nucleotides, or from about 15 nucleotides to about 50 nucleotides.

Still other complexes 60C, 60C', 60C" are shown in FIG. 4C.

In one example, the complex 60C is electrochemically removable and can be used with the working electrode surfaces 32A, 32B, 32C that are unmodified. This example of the complex 60C includes the linking moiety 62A that is capable of attaching to and detaching from the unmodified working electrode surfaces 32A, 32B, 32C, and a hydrogel 68 having i) the linking moiety 62A attached thereto and ii) a plurality of primers 70, 70' attached thereto.

In another example, the complex 60C' is electrochemically removable and can be used with the working electrode surfaces 32A, 32B, 32C that are modified with one member 34A, 34B of the electrochemically responsive transition metal complex binding pair. This example of the complex 60C' includes either the ligand or the transition metal complex (of the electrochemically responsive transition metal complex binding pair) as the linking moiety 62B, and a hydrogel 68 having i) the linking moiety 62B attached thereto and ii) a plurality of primers 70, 70' attached thereto.

In still another example, the complex 60C" is removable via visible light exposure, and can be used with the substrate surfaces 52A, 52B, 52C, 52D that are modified with one member 54A, 54B of the visible light responsive transition metal complex binding pair. This example of the complex 60C" includes either the thioether ligand or the transition metal complex (of the visibly light responsive transition metal complex binding pair) as the linking moiety 62C, and a hydrogel 68 having i) the linking moiety 62C attached thereto and ii) a plurality of primers 70, 70' attached thereto.

Any example of the linking moiety 62A may be used in the complex 60C. The linking moiety 62A may be bonded to any of the functional groups of the hydrogel 68.

The hydrogel 68 may be any gel material that can swell when liquid is taken up and can contract when liquid is removed, e.g., by drying. In an example, the polymeric hydrogel includes an acrylamide copolymer. Some examples of the acrylamide copolymer are represented by the following structure (I):

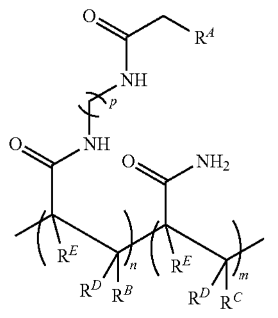

wherein:

$R^A$ is selected from the group consisting of azido, optionally substituted amino, optionally substituted alkenyl, optionally substituted alkyne, halogen, optionally substituted hydrazone, optionally substituted hydrazine, carboxyl, hydroxy, optionally substituted tetrazole, optionally substituted tetrazine, nitrile oxide, nitrone, sulfate, and thiol;

$R^B$ is H or optionally substituted alkyl;

$R^C$, $R^D$, and $R^E$ are each independently selected from the group consisting of H and optionally substituted alkyl;

each of the $-(CH_2)_p-$ can be optionally substituted;

p is an integer in the range of 1 to 50;

n is an integer in the range of 1 to 50,000; and m is an integer in the range of 1 to 100,000.

One specific example of the acrylamide copolymer represented by structure (I) is poly(N-(5-azidoacetamidylpentyl)acrylamide-co-acrylamide, PAZAM.

One of ordinary skill in the art will recognize that the arrangement of the recurring "n" and "m" features in structure (I) are representative, and the monomeric subunits may be present in any order in the polymer structure (e.g., random, block, patterned, or a combination thereof).

The molecular weight of the acrylamide copolymer may range from about 5 kDa to about 1500 kDa or from about 10 kDa to about 1000 kDa, or may be, in a specific example, about 312 kDa.

In some examples, the acrylamide copolymer is a linear polymer. In some other examples, the acrylamide copolymer is a lightly cross-linked polymer.

In other examples, the gel material may be a variation of structure (I). In one example, the acrylamide unit may be replaced with N,N-dimethylacrylamide

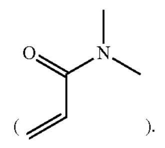

In this example, the acrylamide unit in structure (I) may be replaced with,

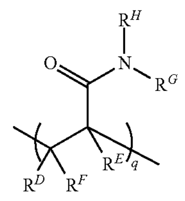

where $R^D$, $R^E$, and $R^F$ are each H or a C1-C6 alkyl, and $R^G$ and $R^H$ are each a C1-C6 alkyl (instead of H as is the case with the acrylamide). In this example, q may be an integer in the range of 1 to 100,000. In another example, the N,N-dimethylacrylamide may be used in addition to the acrylamide unit. In this example, structure (I) may include

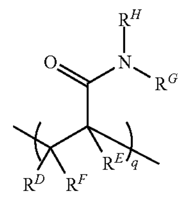

in addition to the recurring "n" and "m" features, where $R^D$, $R^E$, and $R^F$ are each H or a C1-C6 alkyl, and $R^G$ and $R^H$ are each a C1-C6 alkyl. In this example, q may be an integer in the range of 1 to 100,000.

As another example of the polymeric hydrogel, the recurring "n" feature in structure (I) may be replaced with a monomer including a heterocyclic azido group having structure (II):

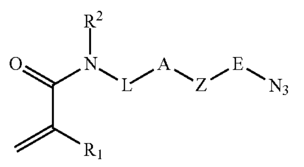

wherein $R^1$ is H or a C1-C6 alkyl; $R_2$ is H or a C1-C6 alkyl; L is a linker including a linear chain with 2 to 20 atoms selected from the group consisting of carbon, oxygen, and nitrogen and 10 optional substituents on the carbon and any nitrogen atoms in the chain; E is a linear chain including 1 to 4 atoms selected from the group consisting of carbon, oxygen and nitrogen, and optional substituents on the carbon and any nitrogen atoms in the chain; A is an N substituted amide with an H or a C1-C4 alkyl attached to the N; and Z is a nitrogen containing heterocycle. Examples of Z include 5 to 10 carbon-containing ring members present as a single cyclic structure or a fused structure. Some specific examples of Z include pyrrolidinyl, pyridinyl, or pyrimidinyl. As still another example, the gel material may include a recurring unit of each of structure (III) and (IV):

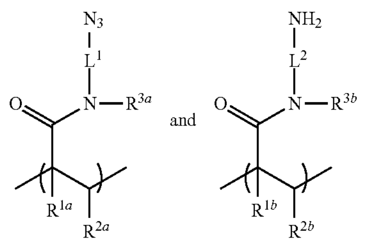

wherein each of $R^{1a}$, $R^{2a}$, $R^{1b}$ and $R^{2b}$ is independently selected from hydrogen, an optionally substituted alkyl or optionally substituted phenyl; each of $R^{3a}$ and $R^{3b}$ is independently selected from hydrogen, an optionally substituted alkyl, an optionally substituted phenyl, or an optionally substituted C7-C14 aralkyl; and each $L^1$ and $L^2$ is independently selected from an optionally substituted alkylene linker or an optionally substituted heteroalkylene linker.

In still another example, the acrylamide copolymer is formed using nitroxide mediated polymerization, and thus at least some of the copolymer chains have an alkoxyamine end group. In the copolymer chain, the term "alkoxyamine end group" refers to the dormant species —$ONR_1R_2$, where each of $R_1$ and $R_2$ may be the same or different, and may independently be a linear or branched alkyl, or a ring structure, and where the oxygen atom is attached to the rest of the copolymer chain. In some examples, the alkoxyamine may also be introduced into some of the recurring acrylamide monomers, e.g., at position $R^A$ in structure (I). As such, in one example, structure (I) includes an alkoxyamine end group; and in another example, structure (I) includes an alkoxyamine end group and alkoxyamine groups in at least some of the side chains.

It is to be understood that other molecules may be used to form the hydrogel 68, as long as they are capable of being functionalized with the desired chemistry, e.g., linker molecule 62A and primers 70, 70'. Some examples of suitable hydrogel 68 materials include functionalized silanes, such as norbornene silane, azido silane, alkyne functionalized silane, amine functionalized silane, maleimide silane, or any other silane having functional groups that can respectively attach the desired chemistry, e.g., linker molecule 62A and primers 70, 70'. Other examples of suitable hydrogel 68 materials include those having a colloidal structure, such as agarose; or a polymer mesh structure, such as gelatin; or a cross-linked polymer structure, such as polyacrylamide polymers and copolymers, silane free acrylamide (SFA), or an azidolyzed version of SFA. Examples of suitable polyacrylamide polymers may be synthesized from acrylamide and an acrylic acid or an acrylic acid containing a vinyl group, or from monomers that form [2+2] photo-cycloaddition reactions. Still other examples of suitable hydrogel 68 materials include mixed copolymers of acrylamides and acrylates. A variety of polymer architectures containing acrylic monomers (e.g., acrylamides, acrylates etc.) may be utilized in the examples disclosed herein, such as branched polymers, including dendrimers (e.g., multi-arm or star polymers), star-shaped or star-block polymers, and the like. For example, the monomers (e.g., acrylamide, acrylamide containing the catalyst, etc.) may be incorporated, either randomly or in block, into the branches (arms) of a dendrimer.

The hydrogel 68 may be formed using any suitable copolymerization process, such as nitroxide mediated polymerization (NMP), reversible addition-fragmentation chain-transfer (RAFT) polymerization, etc.

The primers 70, 70' may be forward and reverse amplification primers. Together the primers 70, 70' enable the amplification of a library template having end adapters that are complementary to the primers 70, 70'. As an example, the primers 70, 70' include P5 and P7 primers. Examples of P5 and P7 primers are used on the surface of commercial flow cells sold by Illumina Inc. for sequencing, for example, on HISEQ™, HISEQX™, MISEQ™, MISEQDX™, MINISEQ™, NEXTSEQ™, NEXTSEQDX™, NOVASEQ™, ISEQ™, GENOME ANALYZER™, and other instrument platforms.

In an example, the P5 primer is:

```
P5: 5' → 3'
                                    (SEQ. ID. NO. 1)
AATGATACGGCGACCACCGAGAUCTACAC
```

The P7 primer may be any of the following:

```
P7 #1: 5' → 3'
                                    (SEQ. ID. NO. 2)
CAAGCAGAAGACGGCATACGAnAT

P7 #2: 5' → 3'
                                    (SEQ. ID. NO. 3)
CAAGCAGAAGACGGCATACnAGAT
```

where "n" is 8-oxoguanine in each of the sequences.

The primers 70, 70' may be terminated, at the 5' end, with a functional group that is capable of single point covalent attachment with a functional group of the hydrogel 68. Examples of terminated primers that may be used include an alkyne terminated primer, a tetrazine terminated primer, an azido terminated primer, an amino terminated primer, an epoxy or glycidyl terminated primer, a thiophosphate terminated primer, a thiol terminated primer, an aldehyde terminated primer, a hydrazine terminated primer, a phosphoramidite terminated primer, and a triazolinedione terminated primer. In some specific examples, a succinimidyl (NHS) ester terminated primer may be reacted with an amine of the hydrogel 68, an aldehyde terminated primer may be reacted with a hydrazine of the hydrogel 68, or an alkyne terminated primer may be reacted with an azide of the hydrogel 68, or an azide terminated primer may be reacted with an alkyne or DBCO (dibenzocyclooctyne) of the hydrogel 68, or an amino terminated primer may be reacted with an activated carboxylate group or NHS ester of the hydrogel 68, or a thiol terminated primer may be reacted with an alkylating reactant (e.g., iodoacetamine or maleimide) of the hydrogel 68, or a phosphoramidite terminated primer may be reacted with a thioether of the polymeric hydrogel 68. While several examples have been provided, it is to be understood that any functional group that can be attached to the primer 70, 70' and that can attach to a functional group of the hydrogel 68 may be used.

As noted above, the complex 60C' includes the hydrogel 68, the primers 70, 70', and the linking moiety 62B instead of the linking moiety 62A. Any example of the hydrogel 68 and the primers 70, 70' may be used. Either the ligand or the transition metal complex of the electrochemically responsive transition metal complex binding pair may be used as the linking moiety 62B. The linking moiety 62B may be bonded to any of the functional groups of the hydrogel 68.

Also as noted above, the complex 60C" includes the hydrogel 68, the primers 70, 70', and the linking moiety 62C instead of the linking moiety 62A. Any example of the hydrogel 68 and the primers 70, 70' may be used. Either the ligand or the transition metal complex of the visible light responsive transition metal complex binding pair may be used as the linking moiety 62C. The linking moiety 62C may be bonded to any of the functional groups of the hydrogel 68. In one specific example, the linking moiety 62C is a thioether and the complex 60C" is a hydrogel 68 having i) the thioether attached thereto and ii) a plurality of primers 70, 70' attached thereto attached thereto.

Still other complexes 60D, 60D', 60D" are shown in FIG. 4D.

In one example, the complex 60D is electrochemically removable and can be used with the working electrode surfaces 32A, 32B, 32C that are unmodified. This example of the complex 60D includes the linking moiety 62A that is capable of attaching to and detaching from the unmodified working electrode surfaces 32A, 32B, 32C, and a particle 72 having i) the linking moiety 62A attached thereto and ii) a cluster of template nucleic acid strands 74 attached thereto.

In another example, the complex 60D' is electrochemically removable and can be used with the working electrode surfaces 32A, 32B, 32C that are modified with one member 34A, 34B of the electrochemically responsive transition metal complex binding pair. This example of the complex 60D' includes either the ligand or the transition metal complex (of the electrochemically responsive transition metal complex binding pair) as the linking moiety 62B, and a particle 72 having i) the linking moiety 62B attached thereto and ii) a cluster of template nucleic acid strands 74 attached thereto.

In still another example, the complex 60D" is removable via visible light exposure, and can be used with the substrate surfaces 52A, 52B, 52C, 52D that are modified with one member 54A, 54B of the visible light responsive transition metal complex binding pair. This example of the complex 60D" includes either the thioether ligand or the transition metal complex (of the visibly light responsive transition metal complex binding pair) as the linking moiety 62C, and a particle 72 having i) the linking moiety 62B attached thereto and ii) a cluster of template nucleic acid strands 74 attached thereto.

Any example of the linking moiety 62A may be used in the complex 60D. The linking moiety 62A may be bonded to any of the functional groups of the particle 72.

The particle 72 may be any suitable material including functional groups that can attach the linking moiety 62A and primers 70, 70' used to generate the cluster of template nucleic acid strands 74. Alternatively, the particle 72 may be coated with the hydrogel 68, which includes functional groups that can attach the linking moiety 62A and primers 70, 70' used to generate the cluster of template nucleic acid strands 74.

Example materials that are useful for the particle 72 include protein scaffolds; glass (e.g., controlled pore glass beads); plastic such as acrylic, polystyrene or a copolymer of styrene and another material, polypropylene, polyethylene, polybutylene, polyurethane or polytetrafluoroethylene (TEFLON®, from Chemours); polysaccharides or cross-linked polysaccharides such as agarose or SEPHAROSE®, from Cytiva Bioprocess); nylon; nitrocellulose; silica or silicon-based materials including silicon and modified silicon; paramagnetic beads; carbon-fibers; metals (e.g., gold, silver, tin, rhodium, ruthenium, palladium, osmium, iridium, platinum, copper, aluminum, etc.); doped semi-metals (e.g., doped silicon); direct bandgap semiconductors (e.g., gallium arsenide); metal composites (two or more of the metals listed above); or the hydrogel 68 disclosed herein. In one example, the particle 72 is selected from the group consisting of silica, any example of the hydrogel 68 disclosed herein, hydrogel 68 coated metal nanoparticles, or protein scaffolds.

The particle 72 can have a shape characterized, for example, as a sphere, oval, microsphere, or other recognized particle shape whether having regular or irregular dimensions.

While not shown in FIG. 4D, the particle 72 initially has primers 70, 70' attached to the surface. In this example, the primers 70, 70' may be terminated, at the 5' end, with a functional group that is capable of single point covalent attachment with a functional group of the particle 72. The primers 70, 70' are used to generate the cluster of template nucleic acid strands 74 shown in FIG. 4D.

To generate the cluster of template nucleic acid strands 74 on the particle 72, library templates may first be prepared from any nucleic acid sample (e.g., a DNA sample or an RNA sample). The DNA nucleic acid sample may be fragmented into single-stranded, similarly sized (e.g., <1000 bp) DNA fragments. The RNA nucleic acid sample may be used to synthesize complementary DNA (cDNA), and the cDNA may be fragmented into single-stranded, similarly sized (e.g., <1000 bp) cDNA fragments. During preparation, adapters may be added to the ends of any of the fragments. Through reduced cycle amplification, different motifs may be introduced in the adapters, such as sequencing primer binding sites, indices, and regions that are complementary to the primers 70, 70' on the particle 72. In some examples, the fragments from a single nucleic acid sample have the same adapters added thereto. The final library templates include the DNA or cDNA fragment and adapters at both ends. The DNA or cDNA fragment represents the portion of the final library template that is to be sequenced.

A plurality of library templates may be introduced to a particle suspension, which includes a liquid carrier and the particles 72 having the primers 70, 70' attached thereto.

Multiple library templates are hybridized, for example, to one of two types of primers 70, 70'.

Amplification of the template nucleic acid strand(s) on the particle 72 may be initiated to form the complex 60D with a cluster of the template stands 74. In one example, amplification involves cluster generation. In one example of cluster generation, the library templates are copied from the hybridized primers by 3' extension using a high-fidelity DNA polymerase. The original library templates are denatured, leaving the copies immobilized all around the particle 72. Isothermal bridge amplification or some other form of amplification may be used to amplify the immobilized copies. For example, the copied templates loop over to hybridize to an adjacent, complementary primer, and a polymerase copies the copied templates to form double stranded bridges, which are denatured to form two single stranded strands. These two strands loop over and hybridize to adjacent, complementary primers and are extended again to form two new double stranded loops. The process is repeated on each template copy by cycles of isothermal denaturation and amplification to create dense clonal clusters on the particle 72. Each cluster of double stranded bridges is denatured. In an example, the reverse strand is removed by specific base cleavage, leaving forward template strands. Clustering results in the formation of several template strands 74 immobilized on the particle 72. This example of clustering is referred to as bridge amplification, and is one example of the amplification that may be performed. It is to be understood that other amplification techniques may be used.

As noted above, the complex 60D' includes the particle 72, the template strands 74, and the linking moiety 62B instead of the linking moiety 62A. Any example of the particle 72 and the template strands 74 may be used. Either the ligand or the transition metal complex of the electrochemically responsive transition metal complex binding pair may be used as the linking moiety 62B. The linking moiety 62B may be bonded to particle 72 via functional groups at the surface of the particle 72.

Also as noted above, the complex 60D" includes the particle 72, the template strands 74, and the linking moiety 62C instead of the linking moiety 62A. Any example of the hydrogel 68 and the primers 70, 70' may be used. Either the ligand or the transition metal complex of the visible light responsive transition metal complex binding pair may be used as the linking moiety 62C. The linking moiety 62C may be bonded to any of the functional groups of the hydrogel 68. In one specific example, the linking moiety 62C is a thioether and the complex 60D" is a hydrogel particle 72 having i) the thioether attached thereto and ii) a cluster of template nucleic acid strands 74 attached thereto.

Still another complex 60E is shown in FIG. 4E. The complex 60E is removable via visible light exposure, and can be used with the substrate surfaces 52A, 52B, 52C, 52D that are modified with one member 54A, 54B of the visible light responsive transition metal complex binding pair. This example of the complex 60E includes the thioether ligand (of the visibly light responsive transition metal complex binding pair) as the linking moiety 62C, and a metal nanoparticle 73 functionalized with i) the ligand and ii) a hydrogel 68' having a plurality of primers 70, 70' attached thereto.

In this example, the metal nanoparticle 73 may be gold, silver, tin, rhodium, ruthenium, palladium, osmium, iridium, platinum, copper, aluminum, etc., the hydrogel 68' may be any example of the hydrogel 68 set forth herein, and the primers 70, 70' may be any of the examples set forth herein.

It is to be understood that any of the complexes 60C through 60E shown with the primers 70, 70' attached may be clustered or partially clustered off flow cell to generate the template nucleic stands 74 before being introduced into the flow cell 10. With partial clustering, amplification cycles are controlled so that the metal nanoparticle 73 is not completely covered with template nucleic stands 74. Similarly, any of the complexes 60C through 60E shown with the template strands 74 may include the primers 70, 70' instead. These examples may be clustered on flow cell to generate the template nucleic stands 74.

Still further, any of the complexes 60A through 60E may also have a polymerase attached thereto. An attached polymerase may be desirable in a single molecule sensing operation. Any suitable polymerase and linking molecule may be used in these examples.

Methods for Regenerating Flow Cell Surfaces Electrochemically

Any of the examples of the flow cell 10 shown in FIG. 2A through FIG. 2C may be used in methods where the working electrode surfaces 32A, 32B, 32C are temporarily modified using an example of the complexes 60 disclosed herein and are regenerable using electrochemistry.

In one example, the method generally includes introducing a first fluid to a flow channel 12 of a flow cell 10 including a working electrode 24A, 24B, 24C having a surface 32A, 32B, 32C that is at least partially exposed to the flow channel 12, the surface 32A, 32B, 32C being unmodified or modified with a first member 34A, 34B of a transition metal complex binding pair, whereby a linking moiety 62A, 62B of a complex 60A, 60B, 60C, 60C', 60D, 60D' present in the first fluid chemically attaches the complex 60A, 60B, 60C, 60C', 60D, 60D' to the surface 32A, 32B, 32C to form a temporarily modified surface of the working electrode 24A, 24B, 24C; performing a sensing operation involving the complex 60A, 60B, 60C, 60C', 60D, 60D' of the temporarily modified surface; and applying a desorption voltage of the linking moiety 62A, 62B to the working electrode 24A, 24B, 24C, thereby detaching the linking moiety 62A, 62B and regenerating the surface 32A, 32B, 32C. Examples of this method are shown and described in reference to FIG. 5 through FIG. 8.

Figure 5:
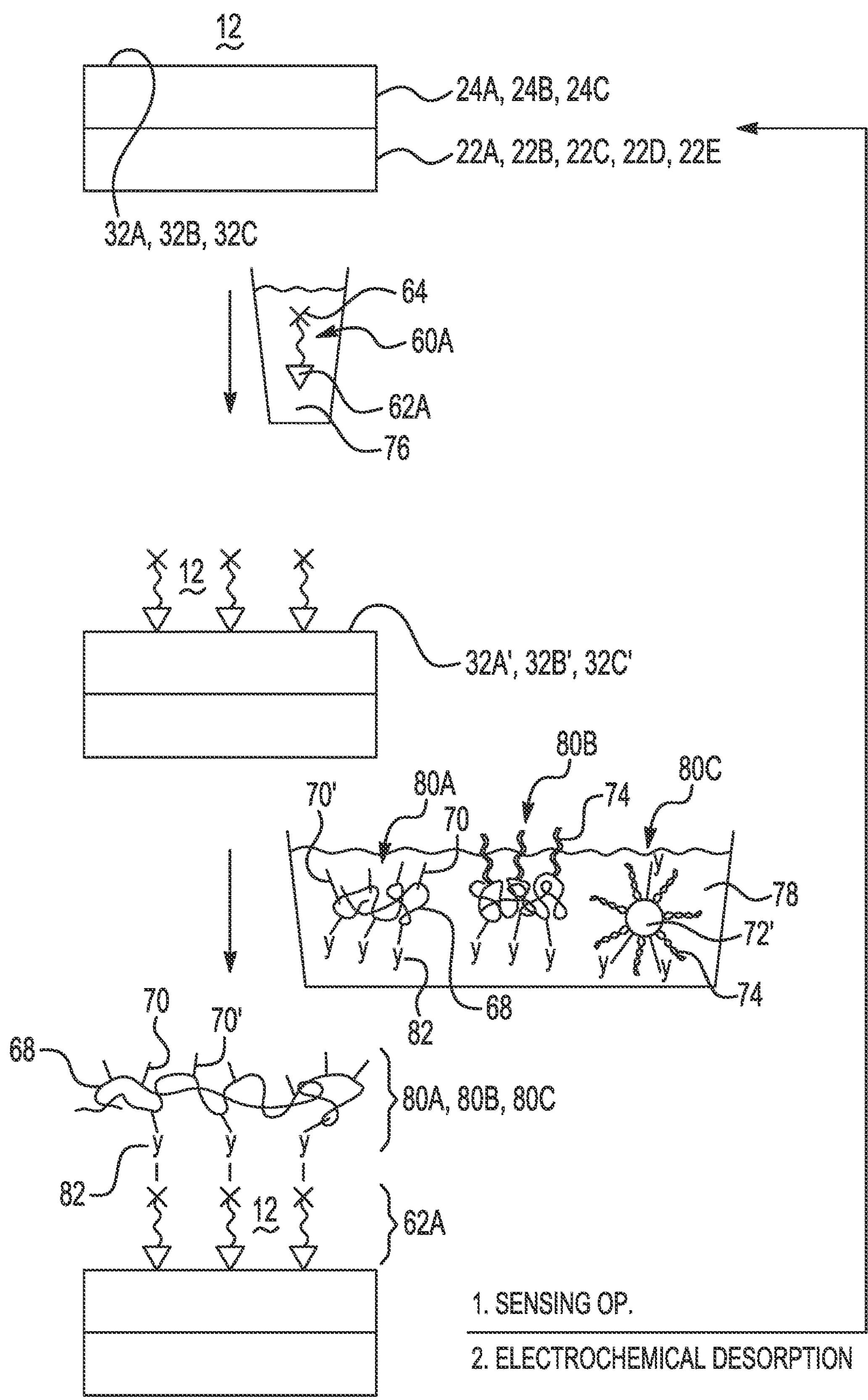
FIG. 5 is a schematic flow diagram illustrating an example of the method disclosed herein involving electrochemical regeneration of the flow cell surface.

One example of this method is schematically shown in FIG. 5. FIG. 5 illustrates a portion of the flow cell 10, which includes the flow channel 12, and the working electrode 24A, 24B, 24C having the surface 32A, 32B, 32C that is at least partially exposed to the flow channel 12. In this example, the working electrode surface 32A, 32B, 32C is unmodified.

In this example method, the complex 60A is present in a first fluid 76. The first fluid 76 may include water and a buffer. Examples of suitable buffers include TRIS (tris (hydroxymethyl)aminomethane or TRIZMA®), Bis-tris methane buffer, ADA buffer (a zwitterionic buffering agent), MES (2-ethanesulfonic acid), MOPS (3-(N-morpholino) propanesulfonic acid), or another acidic buffer. Alternatively, the first fluid 76 may be comprised of an organic solvent with an optional organic-soluble electrolyte, such as a tetraalkylammonium halide.

The first fluid 76 is introduced into the flow channel 12 through the inlet fluidics 36 using the fluidic control system. In one example, the first fluid 76 is pumped from a storage reservoir through a fluid line and into the flow channel 12 through the fluid inlet 14 (not shown in FIG. 5).

Within the flow channel 12, the linking moiety 62A of the complex 60A reacts with the unmodified surface 32A, 32B, 32C. The reaction conditions used will depend upon the linking moiety 62A and the unmodified surface 32A, 32B, 32C. As noted, the reaction may be spontaneous in the presence of the first fluid 76, or may take place in the presence of an applied bias (e.g., diazonium may be attached to an electrode by applying a negative bias between 0 V and −2V). The attachment of the complex 60A to the unmodified surface 32A, 32B, 32C generates one example of the temporarily modified surface 32A', 32B', 32C'.

Once the complex 60A is attached and prior to performing the sensing operation, this example method further comprises introducing, into the flow channel 12, a second fluid 78 that contains additional surface chemistry 80A, 80B, 80C that is to be used in the sensing operation.

In one example of the method shown in FIG. 5, the working electrode surface 32A, 32B, 32C is unmodified, the complex 60A includes the linking moiety 62A and the orthogonal functional group 64 that does not attach to the unmodified surface 32A, 32B, 32C; and prior to performing the sensing operation, the method further comprises introducing, into the flow channel 12, the second fluid 78 including the additional surface chemistry 80A, which includes the hydrogel 68 having i) a plurality of primers 70, 70' attached thereto and ii) a reactive functional group 82 attached thereto that is reactive with the orthogonal functional group 64.

The hydrogel 68 and the primers 70, 70' of the additional surface chemistry 80A may be any of the examples disclosed herein.

The reactive functional group 82 is selected so that it is reactive with the orthogonal functional group 64 of the complex 60A. As examples, the reactive functional group 82 may be an alkyne (e.g., a dialkyne, strained alkynes) or a tetrazine, which covalently attached to an azide orthogonal functional group 64; or the reactive functional group 82 may be a free amine, which covalently attaches to an epoxy orthogonal functional group 64; or the reactive functional group 82 may be a free amine, which covalently attached to an activated carboxylate orthogonal functional group 64; or the reactive functional group 82 may be a hydrazine, which covalently attached to an aldehyde orthogonal functional group 64; or the reactive functional group 82 may be a thioether, which covalently attached to a phosphoramidite orthogonal functional group 64; or the reactive functional group 82 may be a thioether, which covalently attached to an alkylating reagent orthogonal functional group 64. The reactive functional group 82 may also be capable of forming a non-covalent bond with the orthogonal functional group 64 of the complex 60A. For example, the reactive functional group 82 may be streptavidin, which non-covalently bonds to biotin; or the reactive functional group 82 may be a spy-tag, which non-covalently bonds to a spy-catcher.

The reaction of the reactive functional group 82 with the functional group 64 attaches the additional surface chemistry 80A to the temporarily modified surface 32A', 32B', 32C' and renders the temporarily modified surface 32A', 32B', 32C' ready for a sensing operation (shown as #1 in FIG. 5).

While the details are not shown in FIG. 5, the sensing operation in this example method involves amplifying a template nucleic acid strand 74 using the plurality of primers 70, 70' to generate a cluster of template nucleic acid strands 74 on the temporarily modified surface 32A', 32B', 32C'; introducing, into the flow channel 12, a third fluid including a plurality of optically labeled nucleotides; and optically detecting an incorporation event of a respective one of the plurality of optically labeled nucleotides into a nascent strand along at least some of the template nucleic acid strands 74.

Cluster generation on the temporarily modified surface 32A', 32B', 32C' may be performed as described herein using a library template and the primers 70, 70'. In this example, the reagents are introduced into the flow cell 10 and the amplification cycles are carried out using the primers 70, 70' of the additional surface chemistry 80A.

Sequencing primers may then be introduced to the flow cell 10. The sequencing primers hybridize to the template nucleic acid strands 74 on the temporarily modified surface 32A', 32B', 32C'. These sequencing primers render the template strands 74 ready for sequencing.

An incorporation mix including labeled nucleotides may then be introduced into the flow cell 10, e.g., via the inlet 14. In addition to the labeled nucleotides, the incorporation mix may include water, a buffer, and polymerases. When the incorporation mix is introduced into the flow cell 10, the mix enters the flow channel 12, and contacts the anchored and sequence ready template strands 74.

The incorporation mix is allowed to incubate in the flow cell 10, and labeled nucleotides (including optical labels) are incorporated by respective polymerases into the nascent strands along the template strands 74. During incorporation, one of the labeled nucleotides is incorporated, by a respective polymerase, into one nascent strand that extends one sequencing primer and that is complementary to one of the template strands. Incorporation is performed in a template strand dependent fashion, and thus detection of the order and type of labeled nucleotides added to the nascent strand can be used to determine the sequence of the template strand 74. Incorporation occurs in at least some of the template strands 74 across the temporarily modified surface 32A', 32B', 32C' during a single sequencing cycle.

The incorporated labeled nucleotides may include a reversible termination property due to the presence of a 3' OH blocking group, which terminates further sequencing primer extension once the labeled nucleotide has been added. After a desired time for incubation and incorporation, the incorporation mix, including non-incorporated labeled nucleotides, may be removed from the flow cell 10 during a wash cycle. The wash cycle may involve a flow-through technique, where a washing solution (e.g., buffer) is directed into, through, and then out of flow channel 12, e.g., by a pump or other suitable mechanism.

Without further incorporation taking place, the most recently incorporated labeled nucleotides can be detected through an imaging event. During the imaging event, an illumination system may provide an excitation light to the flow cell 10. The optical labels of the incorporated labeled nucleotides emit optical signals in response to the excitation light. These optical signals may be captured using an imaging device.

After imaging is performed, a cleavage mix may then be introduced into the flow cell 10. In an example, the cleavage mix is capable of i) removing the 3' OH blocking group from the incorporated nucleotides, and ii) cleaving the optical label from the incorporated nucleotide. Examples of 3' OH blocking groups and suitable de-blocking agents/components in the cleavage mix may include: ester moieties that can be removed by base hydrolysis; allyl-moieties that can be removed with NaI, chlorotrimethylsilane and $Na_2S_2O_3$ or with Hg(II) in acetone/water; azidomethyl which can be cleaved with phosphines, such as tris(2-carboxyethyl)phosphine (TCEP) or tri(hydroxypropyl)phosphine (THP); acetals, such as tert-butoxy-ethoxy which can be cleaved with acidic conditions; MOM ($—CH_2OCH_3$) moieties that can be cleaved with $LiBF_4$ and $CH_3CN/H_2O$; 2,4-dinitrobenzene sulfenyl which can be cleaved with nucleophiles such as thiophenol and thiosulfate; tetrahydrofuranyl ether which can be cleaved with Ag(I) or Hg(II); and 3' phosphate which can be cleaved by phosphatase enzymes (e.g., polynucleotide kinase). Examples of suitable optical label cleaving agents/components in the cleavage mix may include: sodium periodate, which can cleave a vicinal diol; phosphines, such as tris(2-carboxyethyl)phosphine (TCEP) or tri(hydroxypropyl)phosphine (THP), which can cleave azidomethyl linkages; palladium and THP, which can cleave an allyl; bases, which can cleave ester moieties; or any other suitable cleaving agent.

Additional sequencing cycles may then be performed until the template strands 74 are sequenced.

Once the sensing operation is complete, the desorption voltage of the linking moiety 62A is applied to the working electrode 24A, 24B, 24C (#2 in FIG. 5). An electrolyte solution is introduced into the flow cell 10 so that it is in contact with the working electrode(s) 24A, 24B, 24C and the counter electrode 40 (not shown in FIG. 5). The electrolyte solution may be any solution, aqueous or organic, that has sufficient salt to drive the electrochemistry. A wide range of salt concentrations may be used, e.g., 1 mM<salt<3 M. Example electrolyte solutions include aqueous solutions of sodium salts (e.g., sodium chloride), potassium salts, magnesium salts, manganese salts, etc., or tetraethylammonium tetrafluoroborate ($TEABF_4$) dissolved in acetonitrile or propylene carbonate. Organic electrolytes may also be used, such as tetraalkylammonium halides in organic solvents including acetonitrile, dimethylsulfoxide, tetrahydrofuran, propylene carbonate, methylene chloride or chloroform.

The desorption voltage detaches the linking moiety 62A and the additional surface chemistry 80A attached to the complex 60A, and thus regenerates the surface 32A, 32B, 32C. The desorption voltage will depend upon the linking moiety 62A that is used. In some examples, applying the desorption voltage involves applying a negative bias to the working electrode 24A, 24B, 24C. A sufficiently large negative bias (e.g., −2 V to −3 V) should remove most linking moieties 62A (e.g., acetylene, etc.). In other examples, applying the desorption voltage involves applying a positive bias to the working electrode 24A, 24B, 24C. A sufficiently large positive bias (e.g., +2 V to +3 V) may also be suitable for removing most linking moieties 62A (e.g., diazoniums, etc.).

This example method may further involve introducing a wash fluid to the flow channel 12 after the desorption voltage is applied. This helps to ensure that all of the detached surface chemistry is removed from the flow cell 10.

In another example of the method shown in FIG. 5, the working electrode surface 32A, 32B, 32C is unmodified, the complex 60A includes the linking moiety 62A and the orthogonal functional group 64 that does not attach to the unmodified surface 32A, 32B, 32C; and prior to performing the sensing operation, the method further comprises introducing, into the flow channel 12, the second fluid 78 including the additional surface chemistry 80B, which includes the hydrogel 68 having i) a cluster of template nucleic acid strands 74 attached thereto and ii) a reactive functional group 82 attached thereto that is reactive with the orthogonal functional group 64.

The hydrogel 68 of the additional surface chemistry 80B may be any of the examples disclosed herein, and the template of nucleic acid strands 74 may be generated outside of the flow cell 10 as described herein (e.g., in reference to FIG. 4D). The reactive functional group 82 of the additional surface chemistry 80B may also be any group that is reactive with the orthogonal functional group 64 of the complex 60A.

While FIG. 5 illustrates the additional surface chemistry 80A attached to the temporarily modified surface 32A', 32B', 32C', it is to be understood that in this example, the reaction of the reactive functional group 82 with the functional group 64 attaches the additional surface chemistry 80B to the temporarily modified surface 32A', 32B', 32C'. The attachment of the additional surface chemistry 80B renders the temporarily modified surface 32A', 32B', 32C' ready for a sensing operation.

While the details are not shown in FIG. 5, the sensing operation in this example method involves sequencing the cluster of template nucleic acid strands 74 by introducing, into the flow channel 12, a third fluid including a plurality of optically labeled nucleotides; and optically detecting an incorporation event of a respective one of the plurality of optically labeled nucleotides into a nascent strand along at least some of the template nucleic acid strands 74. Sequencing and optical detection of the incorporation events may take place as described herein.

Once the sensing operation is complete, the desorption voltage of the linking moiety 62A is applied to the working electrode 24A, 24B, 24C. An electrolyte solution is introduced into the flow cell 10 so that it is in contact with the working electrode(s) 24A, 24B, 24C and the counter electrode 40 (not shown in FIG. 5). The desorption voltage detaches the linking moiety 62A and the additional surface chemistry 80B attached to the complex 60A, and thus regenerates the surface 32A, 32B, 32C.

This example method may further involve introducing a wash fluid to the flow channel 12 after the desorption voltage is applied. This helps to ensure that all of the detached surface chemistry is removed from the flow cell 10.

In still another example of the method shown in FIG. 5, the working electrode surface 32A, 32B, 32C is unmodified, the complex 60A includes the linking moiety 62A and the orthogonal functional group 64 that does not attach to the unmodified surface 32A, 32B, 32C; and prior to performing the sensing operation, the method further comprises introducing, into the flow channel 12, the second fluid 78 including the additional surface chemistry 80C, which includes a particle 72' having i) a cluster of template nucleic acid strands 74 attached thereto and ii) a reactive functional group 82 attached thereto that is reactive with the orthogonal functional group 64.

The particle 72' of the additional surface chemistry 80C may be any example of the particle 72 disclosed herein, and the template of nucleic acid strands 74 may be generated outside of the flow cell 10 as described herein (e.g., in reference to FIG. 4D). The reactive functional group 82 of the additional surface chemistry 80C may also be any group that is reactive with the orthogonal functional group 64 of the complex 60A.

While FIG. 5 illustrates the additional surface chemistry 80A attached to the temporarily modified surface 32A', 32B', 32C', it is to be understood that in this example, the reaction of the reactive functional group 82 with the functional group 64 attaches the additional surface chemistry 80C to the temporarily modified surface 32A', 32B', 32C'. The attachment of the additional surface chemistry 80C renders the temporarily modified surface 32A', 32B', 32C' ready for a sensing operation.

While the details are not shown in FIG. 5, the sensing operation in this example method involves sequencing the cluster of template nucleic acid strands 74 by introducing, into the flow channel 12, a third fluid including a plurality of optically labeled nucleotides; and optically detecting an incorporation event of a respective one of the plurality of optically labeled nucleotides into a nascent strand along at least some of the template nucleic acid strands 74. Sequencing and optical detection of the incorporation events may take place as described herein.

Once the sensing operation is complete, the desorption voltage of the linking moiety 62A is applied to the working electrode 24A, 24B, 24C. An electrolyte solution is introduced into the flow cell 10 so that it is in contact with the working electrode(s) 24A, 24B, 24C and the counter electrode 40 (not shown in FIG. 5). The desorption voltage detaches the linking moiety 62A and the additional surface chemistry 80C attached to the complex 60A, and thus regenerates the surface 32A, 32B, 32C.

This example method may further involve introducing a wash fluid to the flow channel 12 after the desorption voltage is applied. This helps to ensure that all of the detached surface chemistry is removed from the flow cell 10.

Figure 6:
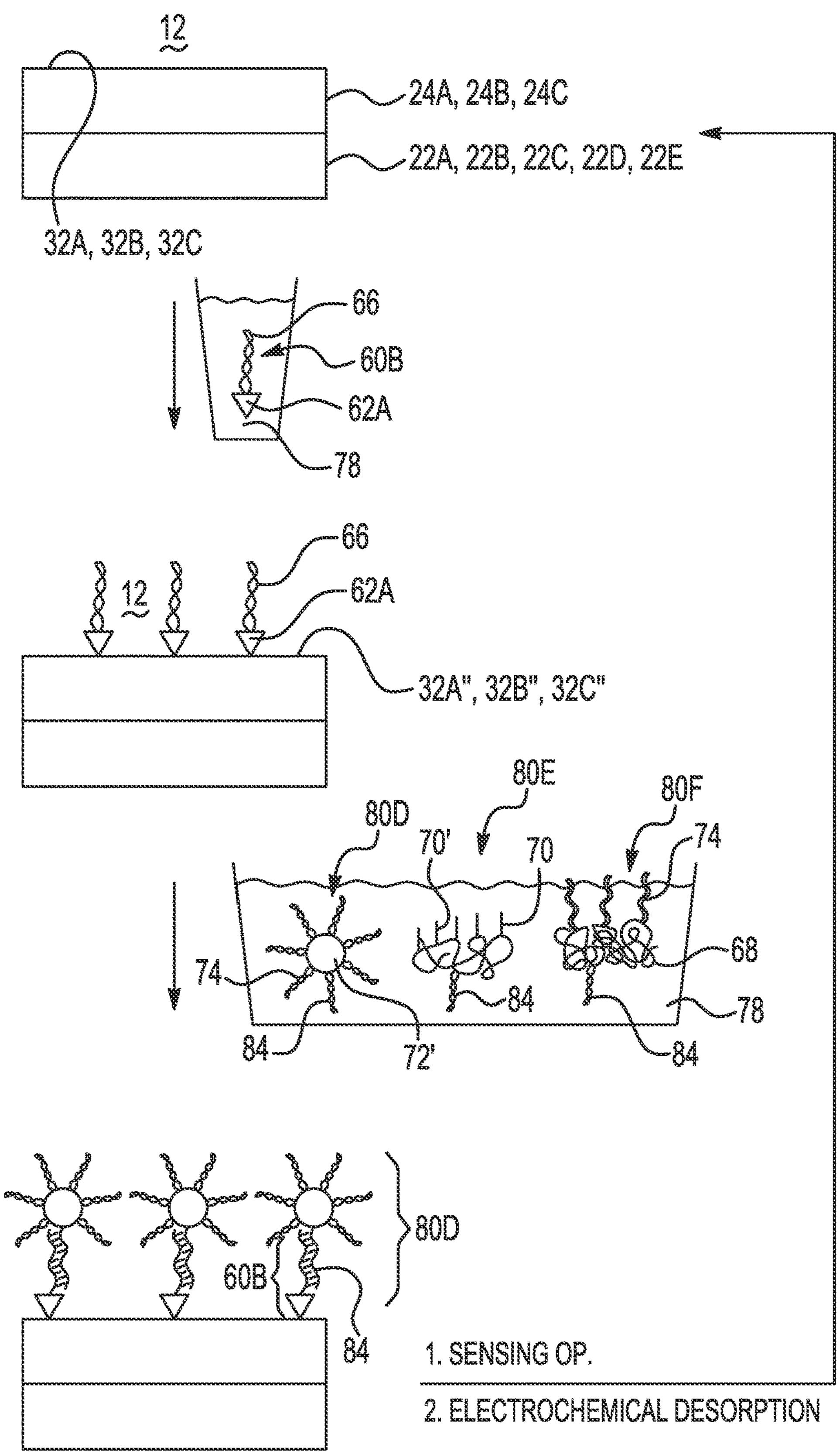
FIG. 6 is a schematic flow diagram illustrating another example of the method disclosed herein involving electrochemical regeneration of the flow cell surface.

Another example of the method is schematically shown in FIG. 6. FIG. 6 illustrates a portion of the flow cell 10, which includes the flow channel 12, and the working electrode 24A, 24B, 24C having the surface 32A, 32B, 32C that is at least partially exposed to the flow channel 12. In this example, the working electrode surface 32A, 32B, 32C is unmodified.

In this example method, the complex 60B is present in a first fluid 76. Any example of the first fluid 76 may be used. The first fluid 76 is introduced into the flow channel 12 through the inlet fluidics 36 using the fluidic control system. In one example, the first fluid 76 is pumped from a storage reservoir through a fluid line and into the flow channel 12 through the fluid inlet 14 (not shown in FIG. 6).

Within the flow channel 12, the linking moiety 62A of the complex 60B reacts with the unmodified surface 32A, 32B, 32C. As mentioned, the reaction conditions used will depend upon the linking moiety 62A and the unmodified surface 32A, 32B, 32C. In some examples, the reaction conditions include the application of bias voltage that initiates attachment of the linking moiety 62A to the unmodified surface 32A, 32B, 32C. The attachment of the complex 60B to the unmodified surface 32A, 32B, 32C generates another example of the temporarily modified surface 32A", 32B", 32C".

Once the complex 60B is attached and prior to performing the sensing operation, this example method further comprises introducing, into the flow channel 12, a second fluid 78 that contains additional surface chemistry 80D, 80E, 80F that is to be used in the sensing operation.

In one example of the method shown in FIG. 6, the working electrode surface 32A, 32B, 32C is unmodified, the complex 60B includes the linking moiety 62A and a capture oligonucleotide 66 attached to the linking moiety 62A; and prior to performing the sensing operation, the method further comprises introducing, into the flow channel 12, the second fluid 78 including the additional surface chemistry 80D, which includes a particle 72' having i) a cluster of template nucleic acid strands 74 attached thereto and ii) an oligonucleotide 84 attached thereto that is complementary to the capture oligonucleotide 66.

The particle 72' of the additional surface chemistry 80D may be any example of the particle 72 disclosed herein, and the template of nucleic acid strands 74 may be generated outside of the flow cell 10 as described herein (e.g., in reference to FIG. 4D).

The oligonucleotide 84 is single stranded nucleic acid sequence that can hybridize to the complementary capture oligonucleotide 66 of the complex 60B attached to the modified working electrode surface 32A", 32B", 32C". The oligonucleotide 84 may have a length ranging from about 10 nucleotides to about 100 nucleotides, or from about 12 nucleotides to about 60 nucleotides, or from about 15 nucleotides to about 50 nucleotides, which depends upon the capture oligonucleotide 66 that is used.

The additional surface chemistry 80D is allowed to incubate in the flow cell 10 at a temperature suitable for hybridizing the oligonucleotide 84 to the capture oligonucleotide 66. As a result of the hybridization, the additional surface chemistry 80D becomes attached to the temporarily modified surface 32A", 32B", 32C" and renders the temporarily modified surface 32A", 32B", 32C" ready for a sensing operation (shown as #1 in FIG. 6).

While the details are not shown in FIG. 6, the sensing operation in this example method involves sequencing the cluster of template nucleic acid strands 74 by introducing, into the flow channel 12, a third fluid including a plurality of optically labeled nucleotides; and optically detecting an incorporation event of a respective one of the plurality of optically labeled nucleotides into a nascent strand along at least some of the template nucleic acid strands 74. Sequencing and optical detection of the incorporation events may take place as described herein.

Once the sensing operation is complete, the desorption voltage of the linking moiety 62A is applied to the working electrode 24A, 24B, 24C. An electrolyte solution is introduced into the flow cell 10 so that it is in contact with the working electrode(s) 24A, 24B, 24C and the counter electrode 40 (not shown in FIG. 6). The desorption voltage detaches the linking moiety 62A and the additional surface chemistry 80D attached to the complex 60B, and thus regenerates the surface 32A, 32B, 32C.

This example method may further involve introducing a wash fluid to the flow channel 12 after the desorption voltage is applied. This helps to ensure that all of the detached surface chemistry is removed from the flow cell 10.

In another example of the method shown in FIG. 6, the working electrode surface 32A, 32B, 32C is unmodified, the complex 60B includes the linking moiety 62A and the capture oligonucleotide 66 attached to the linking moiety 62A; and prior to performing the sensing operation, the method further comprises introducing, into the flow channel 12, the second fluid 78 including the additional surface chemistry 80E, which includes the hydrogel 68 having i) a plurality of primers 70, 70' attached thereto and ii) the oligonucleotide 84 attached thereto that is complementary to the capture oligonucleotide 66.

The hydrogel 68 and the primers 70, 70' of the additional surface chemistry 80E may be any of the examples disclosed herein. As noted above, the oligonucleotide 84 is a single stranded nucleic acid sequence that can hybridize to the complementary capture oligonucleotide 66 of the complex 60B attached to the modified working electrode surface 32A", 32B", 32C".

While FIG. 6 illustrates the additional surface chemistry 80D attached to the temporarily modified surface 32A", 32B", 32C", it is to be understood that in this example, the additional surface chemistry 80E is attached to the temporarily modified surface 32A", 32B", 32C". Additionally, while the details are not shown in FIG. 6, the sensing operation in this example method involves amplifying a template nucleic acid strand 74 using the plurality of primers 70, 70' to generate a cluster of template nucleic acid strands 74 on the temporarily modified surface 32A", 32B", 32C"; introducing, into the flow channel 12, a third fluid including a plurality of optically labeled nucleotides; and optically detecting an incorporation event of a respective one of the plurality of optically labeled nucleotides into a nascent strand along at least some of the template nucleic acid strands 74.

Cluster generation on the temporarily modified surface 32A", 32B", 32C" may be performed as described herein using a library template and the primers 70, 70'. In this example, the reagents are introduced into the flow cell 10 and the amplification cycles are carried out using the primers 70, 70' of the additional surface chemistry 80E.

Sequencing and optical detection of the incorporation events may then take place as described herein.

Once the sensing operation is complete, the desorption voltage of the linking moiety 62A is applied to the working electrode 24A, 24B, 24C. An electrolyte solution is introduced into the flow cell 10 so that it is in contact with the working electrode(s) 24A, 24B, 24C and the counter electrode 40 (not shown in FIG. 6). The desorption voltage detaches the linking moiety 62A and the additional surface chemistry 80E attached to the complex 60B, and thus regenerates the surface 32A, 32B, 32C.

This example method may further involve introducing a wash fluid to the flow channel 12 after the desorption voltage is applied. This helps to ensure that all of the detached surface chemistry is removed from the flow cell 10.

In still another example of the method shown in FIG. 6, the working electrode surface 32A, 32B, 32C is unmodified, the complex 60B includes the linking moiety 62A and a capture oligonucleotide 66 attached to the linking moiety 62A; and prior to performing the sensing operation, the method further comprises introducing, into the flow channel 12, the second fluid 78 including the additional surface chemistry 80F, which includes the hydrogel 68 having i) a cluster of template nucleic acid strands 74 attached thereto and ii) the oligonucleotide 84 attached thereto that is complementary to the capture oligonucleotide 66.

The hydrogel 68 of the additional surface chemistry 80F may be any of the examples disclosed herein, and the template of nucleic acid strands 74 may be generated outside of the flow cell 10 as described herein (e.g., in reference to FIG. 4D). As noted above, the oligonucleotide 84 is a single stranded nucleic acid sequence that can hybridize to the complementary capture oligonucleotide 66 of the complex 60B attached to the modified working electrode surface 32A", 32B", 32C".

While FIG. 6 illustrates the additional surface chemistry 80D attached to the temporarily modified surface 32A", 32B", 32C", it is to be understood that in this example, the hybridization of the oligonucleotide 84 with the capture oligonucleotide 66 attaches the additional surface chemistry 80F to the temporarily modified surface 32A", 32B", 32C". The attachment of the additional surface chemistry 80F renders the temporarily modified surface 32A", 32B", 32C" ready for a sensing operation.

While the details are not shown in FIG. 6, the sensing operation in this example method involves sequencing the cluster of template nucleic acid strands 74 by introducing, into the flow channel 12, a third fluid including a plurality of optically labeled nucleotides; and optically detecting an incorporation event of a respective one of the plurality of optically labeled nucleotides into a nascent strand along at least some of the template nucleic acid strands 74. Sequencing and optical detection of the incorporation events may take place as described herein.

Once the sensing operation is complete, the desorption voltage of the linking moiety 62A is applied to the working electrode 24A, 24B, 24C. An electrolyte solution is introduced into the flow cell 10 so that it is in contact with the working electrode(s) 24A, 24B, 24C and the counter electrode 40 (not shown in FIG. 6). The desorption voltage detaches the linking moiety 62A and the additional surface chemistry 80F attached to the complex 60B, and thus regenerates the surface 32A, 32B, 32C.

This example method may further involve introducing a wash fluid to the flow channel 12 after the desorption voltage is applied. This helps to ensure that all of the detached surface chemistry is removed from the flow cell 10.

Figures 7, 8:
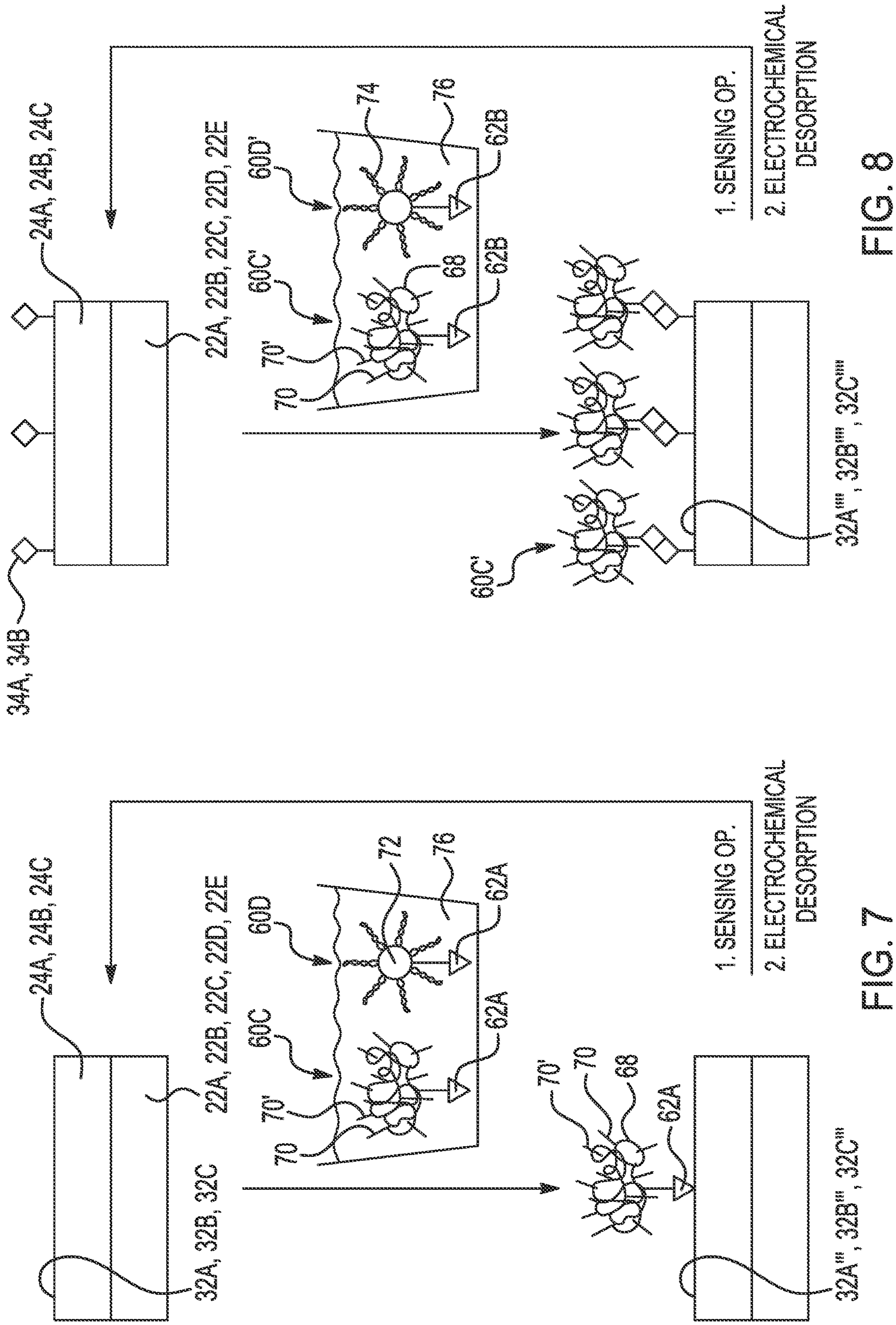
FIG. 7 is a schematic flow diagram illustrating yet another example of the method disclosed herein involving electrochemical regeneration of the flow cell surface.
FIG. 8 is a schematic flow diagram illustrating still another example of the method disclosed herein involving electrochemical regeneration of the flow cell surface.

Still another example of the method is schematically shown in FIG. 7. FIG. 7 illustrates a portion of the flow cell 10, which includes the flow channel 12, and the working electrode 24A, 24B, 24C having the surface 32A, 32B, 32C that is at least partially exposed to the flow channel 12. In this example, the working electrode surface 32A, 32B, 32C is unmodified.

In this example method, the complex 60C or 60D is present in a first fluid 76. Any example of the first fluid 76 disclosed herein may be used. The first fluid 76 is introduced into the flow channel 12 through the inlet fluidics 36 using the fluidic control system. In one example, the first fluid 76 is pumped from a storage reservoir through a fluid line and into the flow channel 12 through the fluid inlet 14 (not shown in FIG. 7).

Within the flow channel 12, the linking moiety 62A of the complex 60C or 60D reacts with the unmodified surface 32A, 32B, 32C. The reaction conditions used will depend upon the linking moiety 62A and the unmodified surface 32A, 32B, 32C. In some examples, the reaction conditions include the application of bias voltage that initiates attachment of the linking moiety 62A to the unmodified surface 32A, 32B, 32C. The attachment of the complex 60C or 60D to the unmodified surface 32A, 32B, 32C generates another example of the temporarily modified surface 32A'", 32B'", 32C'".

Once the complex 60C or 60D is attached, the sensing operation may be performed (#1 in FIG. 7). The sensing operation varies depending upon the complex 60C, 60D that is used.

In one example, the working electrode surface 32A, 32B, 32C is unmodified, and the complex 60C includes the hydrogel 68 having i) the linking moiety 62A attached thereto and ii) a plurality of primers 70, 70' attached thereto. In this example, the hydrogel 68, the primers 70, 70', and the linking moiety 62A may be any of the examples disclosed herein.

While the details are not shown in FIG. 7, the sensing operation in this example method involves amplifying a template nucleic acid strand 74 using the plurality of primers 70, 70' to generate a cluster of template nucleic acid strands 74 on the temporarily modified surface 32A'", 32B'", 32C'"; introducing, into the flow channel 12, a second fluid including a plurality of optically labeled nucleotides; and optically detecting an incorporation event of a respective one of the plurality of optically labeled nucleotides into a nascent strand along at least some of the template nucleic acid strands 74.

Cluster generation on the temporarily modified surface 32A'", 32B'", 32C'" may be performed as described herein using a library template and the primers 70, 70'. In this example, the reagents are introduced into the flow cell 10 and the amplification cycles are carried out using the primers 70, 70' of the complex 60C.

Sequencing and optical detection of the incorporation events may then take place as described herein.

Once the sensing operation is complete, the desorption voltage of the linking moiety 62A is applied to the working electrode 24A, 24B, 24C. An electrolyte solution is introduced into the flow cell 10 so that it is in contact with the working electrode(s) 24A, 24B, 24C and the counter electrode 40 (not shown in FIG. 7). The desorption voltage detaches the linking moiety 62A and the surface chemistry attached to the complex 60C. This regenerates the unmodified working electrode surface 32A, 32B, 32C.

This example method may further involve introducing a wash fluid to the flow channel 12 after the desorption voltage is applied. This helps to ensure that all of the detached surface chemistry is removed from the flow cell 10.

In another example, the working electrode surface 32A, 32B, 32C is unmodified, and the complex 60D includes the hydrogel 68 having i) the linking moiety 62A attached thereto and ii) a plurality of primers 70, 70' attached thereto. In this example, the hydrogel 68, the primers 70, 70', and the linking moiety 62A may be any of the examples disclosed herein.

In one example, the working electrode surface 32A, 32B, 32C is unmodified, and the complex 60D includes the particle 72 having i) the linking moiety 62A attached thereto and ii) a cluster of template strands 74 attached thereto. In this example, the hydrogel 68 and the linking moiety 62A may be any of the examples disclosed herein. The template of nucleic acid strands 74 may be generated outside of the flow cell 10 as described herein (e.g., in reference to FIG. 4D).

While the details are not shown in FIG. 7, the sensing operation in this example method involves sequencing the cluster of template nucleic acid strands 74 by introducing, into the flow channel 12, a second fluid including a plurality of optically labeled nucleotides; and optically detecting an incorporation event of a respective one of the plurality of optically labeled nucleotides into a nascent strand along at least some of the template nucleic acid strands 74. Sequencing and optical detection of the incorporation events may then take place as described herein.

Once the sensing operation is complete, the desorption voltage of the linking moiety 62A is applied to the working electrode 24A, 24B, 24C. An electrolyte solution is introduced into the flow cell 10 so that it is in contact with the working electrode(s) 24A, 24B, 24C and the counter electrode 40 (not shown in FIG. 7). The desorption voltage detaches the linking moiety 62A and the surface chemistry attached to the complex 60D. This regenerates the unmodified working electrode surface 32A, 32B, 32C.

This example method may further involve introducing a wash fluid to the flow channel 12 after the desorption voltage is applied. This helps to ensure that all of the detached surface chemistry is removed from the flow cell 10.

Still another example of the method is schematically shown in FIG. 8. FIG. 8 illustrates a portion of the flow cell 10, which includes the flow channel 12, and the working electrode 24A, 24B, 24C having the surface 32A, 32B, 32C that is at least partially exposed to the flow channel 12. In this example, the working electrode surface 32A, 32B, 32C is modified with one member 34A, 34B of the electrochemically reversible transition metal binding pair.

In this example method, the complex 60C' or 60D' is used, which includes the linking moiety 62B. As described herein in reference to FIG. 4C and FIG. 4D, the linking moiety 62B includes the other member of the electrochemically reversible transition metal binding pair, which can bind to the member 34A, 34B.

The complex 60C' or 60D' is present in the first fluid 76, which may be any of the examples disclosed herein. The first fluid 76 containing the complex 60C' or 60D' is introduced into the flow channel 12 through the inlet fluidics 36 using the fluidic control system as described herein.

Within the flow channel 12, the linking moiety 62B of the complex 60C' or 60D' binds to the member 34A, 34B. The reaction conditions used will depend upon the transition metal binding pair. In some examples, the reaction conditions include the application of bias voltage that initiates attachment of the linking moiety 62B to the member 34A, 34B. The attachment of the linking moiety 62B of the complex 60C' or 60D' to the member 34A, 34B generates yet another example of the temporarily modified surface 32A"", 32B"", 32C"".

Once the binding pair is formed on the temporarily modified surface 32A"", 32B"", 32C"", the sensing operation may be performed (#1 in FIG. 8). The sensing operation varies depending upon the complex 60C', 60D' that is used.

In one example involving the complex 60C', the working electrode surface 32A, 32B, 32C is modified with the first member 34A, 34B of the transition metal complex binding pair and the first member 34A, 34B of the transition metal complex binding pair is a ligand; the linking moiety 62B is a transition metal complex and the transition metal complex is the second member of the transition metal complex binding pair; and the complex 60C' includes the hydrogel 68 having i) the transition metal complex attached thereto and ii) a plurality of primers 70, 70' attached thereto.

In this example, the first member 34A, 34B of the transition metal complex binding pair attached to the working electrode surface 32A, 32B, 32C may be pyridine, and the transition metal complex (i.e., linking moiety 62B) attached to the hydrogel 68 may be a zinc porphyrin complex. In this example, the complex 60C' functionalizes the surface 32A, 32B, 32C when pyridine complexes the zinc of the zinc porphyrin complex.

While the details are not shown in FIG. 8, the sensing operation in this example method involves amplifying a template nucleic acid strand 74 using the plurality of primers 70, 70' to generate a cluster of template nucleic acid strands 74 on the temporarily modified surface 32A"", 32B"", 32C""; introducing, into the flow channel 12, a second fluid including a plurality of optically labeled nucleotides; and optically detecting an incorporation event of a respective one of the plurality of optically labeled nucleotides into a nascent strand along at least some of the template nucleic acid strands 74.

Cluster generation on the temporarily modified surface 32A"", 32B"", 32C"" may be performed as described herein using a library template and the primers 70, 70'. In this example, the reagents are introduced into the flow cell 10 and the amplification cycles are carried out using the primers 70, 70' of the complex 60C'.

Sequencing and optical detection of the incorporation events may then take place as described herein.

Once the sensing operation is complete, the desorption voltage of the linking moiety 62B is applied to the working electrode 24A, 24B, 24C. An electrolyte solution is introduced into the flow cell 10 so that it is in contact with the working electrode(s) 24A, 24B, 24C and the counter electrode 40 (not shown in FIG. 8). The desorption voltage will depend upon the linking moiety 62B that is used. In some examples, applying the desorption voltage involves applying a negative bias to the working electrode 24A, 24B, 24C. In other examples, applying the desorption voltage involves applying a positive bias to the working electrode 24A, 24B, 24C. In the example with the pyridine and zinc porphyrin complex binding pair, the desorption voltage is a voltage that reduces zinc 1 to zinc 0.

The desorption voltage detaches the linking moiety 62B from the first member 34A, 34B. As such, the surface chemistry attached through the linking moiety 62B is removed. This regenerates the working electrode surface 32A, 32B, 32C modified with the first member 34A, 34B.

This example method may further involve introducing a wash fluid to the flow channel 12 after the desorption voltage is applied. This helps to ensure that all of the detached surface chemistry is removed from the flow cell 10.

In another example involving the complex 60D, the working electrode surface 32A, 32B, 32C is modified with the first member 34A, 34B of the transition metal complex binding pair, the first member 34A, 34B of the transition metal complex binding pair is a transition metal complex; the linking moiety 62B is a ligand, and the ligand is a second member of the transition metal complex binding pair; and the complex 60D' includes a metal nanoparticle functionalized with i) the ligand (linking moiety 62B) and ii) a hydrogel 68 having a cluster of template nucleic acid strands 74 attached thereto In this example, the first member 34A, 34B of the transition metal complex binding pair attached to the working electrode surface 32A, 32B, 32C may be ferrocenyl-poly(propylene imine) dendrimers, and the ligand (i.e., linking moiety 62B) attached to the hydrogel 68 may be a β-cyclodextrin. In this example, the complex 60D' functionalizes the surface 32A, 32B, 32C using electrochemical reduction of the ferrocenyl end groups.

While the details are not shown in FIG. 8, the sensing operation in this example method involves sequencing the cluster of template nucleic acid strands 74 by introducing, into the flow channel 12, a second fluid including a plurality of optically labeled nucleotides; and optically detecting an incorporation event of a respective one of the plurality of optically labeled nucleotides into a nascent strand along at least some of the template nucleic acid strands 74. Sequencing and optical detection of the incorporation events may then take place as described herein.

Once the sensing operation is complete, the desorption voltage of the linking moiety 62B is applied to the working electrode 24A, 24B, 24C. An electrolyte solution is introduced into the flow cell 10 so that it is in contact with the working electrode(s) 24A, 24B, 24C and the counter electrode 40 (not shown in FIG. 8). The desorption voltage detaches the linking moiety 62B from the first member 34A, 34B. As such, the surface chemistry attached through the linking moiety 62B is removed. This regenerates the working electrode surface 32A, 32B, 32C modified with the first member 34A, 34B. In the example with the ferrocenyl-poly (propylene imine) dendrimer and β-cyclodextrin binding pair, the desorption voltage is a voltage that oxidizes the ferrocenyl end groups. In some examples, the desorption voltage detaches the linking moiety 62B from the first member 34A, 34B and detaches the first member 34A, 34B from the working electrode surface 32A, 32B, 32C. In these instances, the first member 34A, 34B may be introduced and attached to the working electrode surface 32A, 32B, 32C (e.g., through a silane linker, etc.) when additional surface chemistry is added to the flow cell 10.

This example method may further involve introducing a wash fluid to the flow channel 12 after the desorption voltage is applied. This helps to ensure that all of the detached surface chemistry is removed from the flow cell 10.

Unlike chemical cleaning methods (e.g., the introduction of a strong acid or base, etc.), the electrochemical desorption methods described in reference to FIG. 5 through FIG. 8 do not degrade bulk materials on the working electrode surface 32A, 32B, 32C, rather, they degrade the interface (e.g., linking moiety 62A, 62B) between the working electrode surface 32A, 32B, 32C and the surface chemistry. In any of these examples, removal of surface chemistry can also be made more efficient by utilizing surface chemistry that possess a net charge that can be repelled away from the surface during application of the desorption bias.

Still another example of a method involving electrochemical regeneration includes introducing a first fluid 76 to a flow channel 12 of a flow cell 10 including a working electrode 24A, 24B, 24C having an unmodified surface 32A, 32B, 32C that is at least partially exposed to the flow channel 12, whereby a linking moiety 62A of a complex 60A, 60B, 60C, 60D, present in the first fluid 76 chemically attaches the complex 60A, 60B, 60C, 60D, to the surface 32A, 32B, 32C to form a temporarily modified surface (e.g., 32A', 32A", 32A"') of the working electrode 24A, 24B, 24C; performing a sensing operation involving the complex 60A, 60B, 60C, 60D of the temporarily modified surface (e.g., 32A', 32A", 32A"'); introducing an electrolyte solution to the flow cell 10; and applying a voltage to the working electrode 24A, 24B, 24C in the presence of the electrolyte solution, thereby removing a layer of the working electrode 24A, 24B, 24C and regenerating the unmodified surface 32A, 32B, 32C.

The methods for attaching the complex 60A, 60B, 60C, 60D to the unmodified surface 32A, 32B, 32C may be performed as described herein in reference to FIG. 5 through FIG. 7.

In this additional example, rather than degrading the interface (e.g., linking moiety 62A, 62B) between the working electrode surface 32A, 32B, 32C and the surface chemistry, the surface bound groups may be removed electrochemically by corroding away a thin layer of the working electrode surface 32A, 32B, 32C. The bias applied for corroding a thin layer of the working electrode surface 32A, 32B, 32C will depend on the particular metal and the concentration of salt in the solution. In some instances, corrosion is possible at zero bias, or may require application of some positive bias between 0 to +1V. In instances when corrosion occurs spontaneously at 0 bias, a negative bias may be applied for corrosion protection during the sensing operation in order to preserve the surface chemistry when it is being introduced and utilized.

This removes the surface chemistry since the metal at the working electrode surface 32A, 32B, 32C that is bound to the surface chemistry leaves the surface as ions.

In this example, the flow cell 10 would have a certain lifetime that is related to the initial thickness of the working electrode 24A, 24B, 24C and the loss in thickness per cleaning cycle.

When the flow cell 10 includes the second working electrode 42A, 42B, 42C, any of the methods may also involve applying a voltage to the second working electrode 42A, 42B, 42C to repel the surface chemistry from attaching during the introduction of the surface chemistry. As such, some examples of the method involve applying the desorption voltage of the linking moiety 62A, 62B to the second working electrode 42A, 42B, 42C as the first fluid 76 is introduced, thereby repelling the complex 60A, 60B, 60C, 60C', 60D, 60D' from the interstitial regions 30A, 30B, 30C. When the flow cell 10 includes the second working electrode 42A, 42B, 42C, any of the methods may also involve applying a voltage to the second working electrode 42A, 42B, 42C to aid in cleaning the second working electrode 42A, 42B, 42C during desorption of the surface chemistry. As such, some examples of the method involve applying the desorption voltage of the linking moiety 62A, 62B to the second working electrode 42A, 42B, 42C after the sensing operation.

Methods for Regenerating Flow Cell Surfaces with Visible Light

Any of the examples of the flow cell 10 shown in FIG. 3A and FIG. 3B may be used in methods where the substrate surfaces 52A, 52B, 52C, 52D are temporarily modified using an example of the complexes 60C", 60D", 60E disclosed herein and are regenerable using visible light exposure.

In one example, the method generally includes introducing a first fluid 76 to a flow channel 12 of a flow cell 10 including a surface 52A, 52B, 52C, 52D of a substrate 22F, 22G, 22H, 22I that is at least partially exposed to the flow channel 12, the surface 52A, 52B, 52C, 52D being modified with a visible light responsive first member 54A, 54B of a transition metal complex binding pair, whereby a linking moiety 62C of a complex 60C", 60D", 60E present in the first fluid 76 chemically attaches the complex 60C", 60D", 60E to the surface 52A, 52B, 52C, 52D to form a temporarily modified surface of the substrate 22F, 22G, 22H, 22I; performing a sensing operation involving the complex 60C", 60D", 60E of the temporarily modified surface; and exposing the temporarily modified surface to visible light, thereby detaching the linking moiety 62C and regenerating the surface 52A, 52B, 52C, 52D. Examples of this method are shown and described in reference to FIG. 9.

Figure 9:
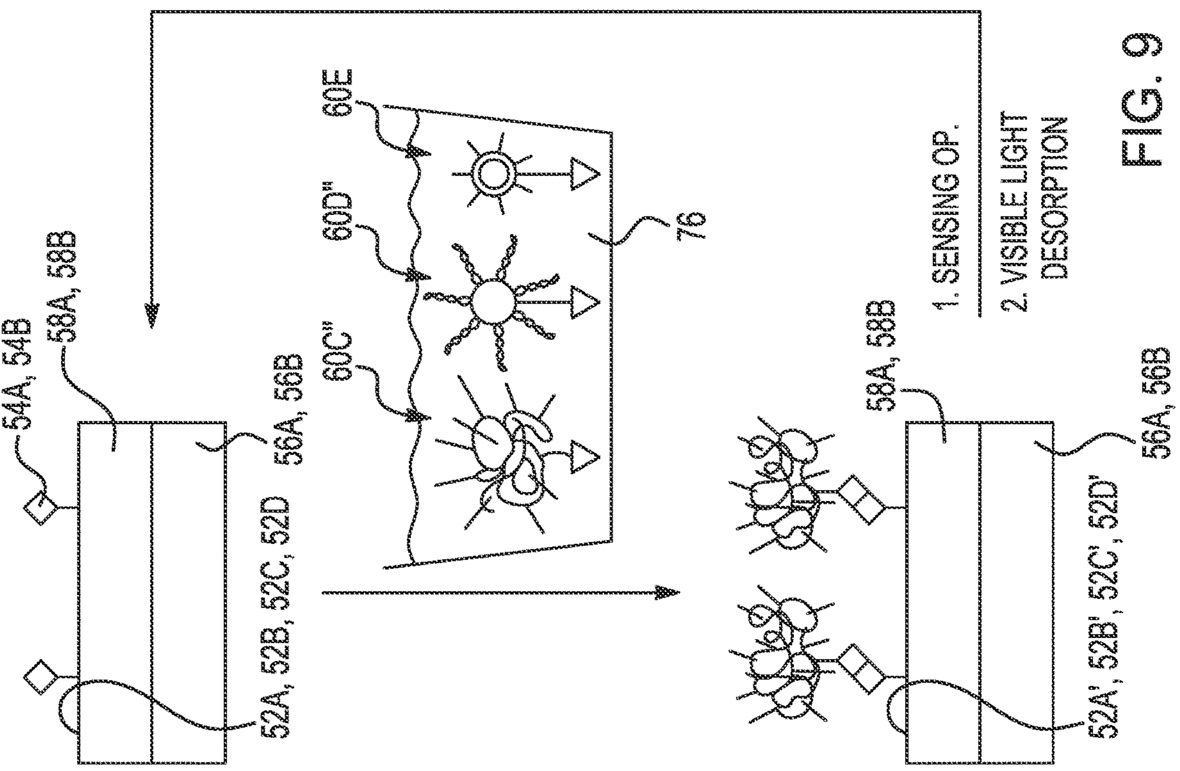
FIG. 9 is a schematic flow diagram illustrating an example of the method disclosed herein involving visible light regeneration of the flow cell surface.

FIG. 9 illustrates a portion of the flow cell 10, which includes the flow channel 12, and the substrate 22F, 22G, 22H, 22I having the surface 52A, 52B, 52C, 52D that is at least partially exposed to the flow channel 12. In this example, the substrate surface 52A, 52B, 52C, 52D is modified with one member 54A, 54B of the visible light responsive transition metal binding pair.

In this example method, the complex 60C" or 60D" or 60E is used, which includes the linking moiety 62C. As described herein in reference to FIG. 4C through FIG. 4E, the linking moiety 62C includes the other member of the visible light responsive transition metal binding pair, which can bind to the member 54A, 54B.

The complex 60C" or 60D" or 60E is present in the first fluid 76, which may be any of the examples disclosed herein. The first fluid 76 containing the complex 60C" or 60D" or 60E is introduced into the flow channel 12 through the inlet fluidics 36 using the fluidic control system as described herein.

Within the flow channel 12, the linking moiety 62C of the complex 60C" or 60D" or 60E binds to the member 54A, 54B. The reaction conditions used will depend upon the transition metal binding pair. In an example, the reaction may be performed in chloroform with from about 20 minutes to about 30 minutes of light exposure. The attachment of the linking moiety 62C of the complex 60C" or 60D" or 60E to the member 54A, 54B generates an example of the temporarily modified surface 52A', 52B', 52C', 52D'. In any of these examples, the first member 54A, 54B may be a hydrolyzed ruthenium complex, and the linking moiety 62C may be a thioether. In these examples, the complex 60C" or 60D" or 60E functionalizes the substrate surface 52A, 52B, 52C, 52D when the hydrolyzed ruthenium complex complexes the thiol of the thioether linking moiety 62C.

Once the binding pair is formed on the temporarily modified surface 52A', 52B', 52C', 52D', the sensing operation may be performed (#1 in FIG. 9). The sensing operation varies depending upon the complex 60C", 60D", 60E that is used.

In an example involving the complex 60C", the linking moiety 62C is the thioether and the complex 60C" is the hydrogel 68 having i) the thioether attached thereto and ii) a plurality of primers 70, 70' attached thereto.

The hydrogel 68 and primers 70, 70' may be any of the examples disclosed herein. The thioether may be attached to a suitable functional group of the hydrogel 68.

While the details are not shown in FIG. 9, the sensing operation in this example method involves amplifying a template nucleic acid strand 74 using the plurality of primers 70, 70' to generate a cluster of template nucleic acid strands 74 on the temporarily modified surface 52A', 52B', 52C', 52D'; introducing, into the flow channel 12, a second fluid including a plurality of optically labeled nucleotides; and optically detecting an incorporation event of a respective one of the plurality of optically labeled nucleotides into a nascent strand along at least some of the template nucleic acid strands 74.

Cluster generation on the temporarily modified surface 52A', 52B', 52C', 52D' may be performed as described herein using a library template and the primers 70, 70'. In this example, the reagents are introduced into the flow cell 10 and the amplification cycles are carried out using the primers 70, 70' of the complex 60C".

Sequencing and optical detection of the incorporation events may then take place as described herein.

Once the sensing operation is complete, the temporarily modified surface 52A', 52B', 52C', 52D' may be exposed to visible light. Visible light exposure may be performed using a light source (e.g., a laser) that emits wavelengths that induce the disassociation of the thioether linking moiety 62C, and thus the complex 60C". The time for visible light exposure may depend upon the power of the light source. A higher power light source may involve a shorter exposure time and a lower power light source may involve a longer exposure time.

The visible light disassociates the linking moiety 62C from the first member 54A, 54B. As such, the surface chemistry attached through the linking moiety 62C is removed. This regenerates the substrate surface 52A, 52B, 52C, 52D modified with the first member 54A, 54B.

This example method may further involve introducing a wash fluid to the flow channel 12 after the visible light exposure. This helps to ensure that all of the detached surface chemistry is removed from the flow cell 10.

In an example involving the complex 60D", the linking moiety 62C is the thioether and the complex 60D" is the hydrogel 68 having i) the thioether attached thereto and ii) a cluster of template strands 74 attached thereto.

The hydrogel 68 may be any of the examples disclosed herein, and the template of nucleic acid strands 74 may be generated outside of the flow cell 10 as described herein (e.g., in reference to FIG. 4D).

While the details are not shown in FIG. 9, the sensing operation in this example method involves sequencing the cluster of template strands 74 by introducing, into the flow channel 12, a second fluid including a plurality of optically labeled nucleotides; and optically detecting an incorporation event of a respective one of the plurality of optically labeled nucleotides into a nascent strand along at least some of the template nucleic acid strands 74. Sequencing and optical detection of the incorporation events may then take place as described herein.

Once the sensing operation is complete, the temporarily modified surface 52A', 52B', 52C', 52D' may be exposed to visible light. Visible light exposure may be performed using a light source (e.g., a laser) that emits wavelengths that induce the disassociation of the linking moiety 62C, and thus the complex 60D". The time for visible light exposure may depend upon the power of the light source.

The visible light disassociates the linking moiety 62C from the first member 54A, 54B. As such, the surface chemistry attached through the linking moiety 62C is removed. This regenerates the substrate surface 52A, 52B, 52C, 52D modified with the first member 54A, 54B.

This example method may further involve introducing a wash fluid to the flow channel 12 after the visible light exposure. This helps to ensure that all of the detached surface chemistry is removed from the flow cell 10.

In an example involving the complex 60E, the linking moiety 62C is the thioether and the complex 60E is the metal nanoparticle 73 functionalized with i) the thioether and ii) a plurality of primers 70, 70' attached thereto.

The metal nanoparticle 73 and the plurality of primers 70, 70' may be any example disclosed herein. The thioether may be attached to a suitable functional group of the hydrogel 68.

While the details are not shown in FIG. 9, the sensing operation in this example method involves amplifying a template nucleic acid strand 74 using the plurality of primers 70, 70' to generate a cluster of template nucleic acid strands 74 on the temporarily modified surface 52A', 52B', 52C', 52D'; introducing, into the flow channel 12, a second fluid including a plurality of optically labeled nucleotides; and optically detecting an incorporation event of a respective one of the plurality of optically labeled nucleotides into a nascent strand along at least some of the template nucleic acid strands 74.

Cluster generation on the temporarily modified surface 52A', 52B', 52C', 52D' may be performed as described herein using a library template and the primers 70, 70'. In this example, the reagents are introduced into the flow cell 10 and the amplification cycles are carried out using the primers 70, 70' of the complex 60E.

Sequencing and optical detection of the incorporation events may then take place as described herein.

Once the sensing operation is complete, the temporarily modified surface 52A', 52B', 52C', 52D' may be exposed to visible light. Visible light exposure may be performed using a light source (e.g., a laser) that emits wavelengths that induce the disassociation of the linking moiety 62C, and thus the complex 60E. The time for visible light exposure may depend upon the power of the light source.

The visible light disassociates the linking moiety 62C from the first member 54A, 54B. As such, the surface chemistry attached through the linking moiety 62C is removed. This regenerates the substrate surface 52A, 52B, 52C, 52D modified with the first member 54A, 54B.

This example method may further involve introducing a wash fluid to the flow channel 12 after the visible light exposure. This helps to ensure that all of the detached surface chemistry is removed from the flow cell 10.

Kits

Any example of the flow cell 10 disclosed herein may be included with flow cell surface chemistry fluid(s) as part of a kit. One example of a kit includes i) a flow cell 10, including: a flow channel 12; a working electrode 24A, 24B, 24C having a surface 32A, 32B, 32C that is at least partially exposed to the flow channel 12, the surface 32A, 32B, 32C being unmodified or modified with a first member 34A, 34B of a transition metal complex binding pair; and a counter electrode 40 electrically connected to the working electrode 24A, 24B, 24C; and ii) a flow cell surface chemistry fluid, including: a liquid carrier (e.g., fluid 76); and a complex 60A, 60B, 60C, 60C', 60D, 60D' including a linking moiety 62A, 62B that is to chemically attach to the unmodified surface or to the first member 34A, 34B of the transition metal complex binding pair, and that is to desorb from the unmodified surface or from the first member 34A, 34B of the transition metal complex binding pair when exposed to a desorption voltage. Examples of the flow cell 10 in this kit may also include the second working electrode 42A, 42B, 42C in any of the configurations set forth herein, the counter electrode 40 in any of the configurations set forth herein, and the controller in any of the configurations set forth herein.

In one example of this kit, the surface 32A, 32B, 32C is unmodified; the complex 60A includes the linking moiety 62A and an orthogonal functional group 64 that does not attach to the unmodified surface 32A, 32B, 32C; and the kit further includes a second fluid (e.g., fluid 78) including the hydrogel 68 having i) the plurality of primers 70, 70' attached thereto and ii) a reactive functional group 82 attached thereto that is reactive with the orthogonal functional group 64. This example kit may also include a third fluid including a plurality of optically labeled nucleotides.

In another example of this kit, the surface 32A, 32B, 32C is unmodified; the complex 60A includes the linking moiety 62A and an orthogonal functional group 64 that does not attach to the unmodified surface 32A, 32B, 32C; and the kit further includes a second fluid (e.g., fluid 78) including the particle 72 having i) the cluster of template strands 74 attached thereto and ii) a reactive functional group 82 attached thereto that is reactive with the orthogonal functional group 64. This example kit may also include a third fluid including a plurality of optically labeled nucleotides.

In still another example of this kit, the surface 32A, 32B, 32C is unmodified; the complex 60B includes the linking moiety 62A and a capture oligonucleotide 66 attached to the linking moiety 62A; and the kit further includes a second fluid (e.g., fluid 78) including the particle 72 having i) the cluster of template strands 74 attached thereto and ii) an oligonucleotide 84 attached thereto that is complementary to the capture oligonucleotide 66. This example kit may also include a third fluid including a plurality of optically labeled nucleotides.

In yet another example of this kit, the surface 32A, 32B, 32C is unmodified; and the complex 60C includes a particle 72 having i) the linking moiety 62A attached thereto and ii) a plurality of primers 70, 70' attached thereto. This example kit may also include a second fluid with reagents for generating the template strands 74 and a third fluid including a plurality of optically labeled nucleotides.

In still another example of this kit, the surface 32A, 32B, 32C is unmodified; and the complex 60D includes a particle 72 having i) the linking moiety 62A attached thereto and ii) a cluster of template nucleic acid strands 74 attached thereto. This example kit may also include a second fluid including a plurality of optically labeled nucleotides.

In another example of this kit, the surface 32A, 32B, 32C is modified with the first member 34A, 34B of the transition metal complex binding pair; the first member 34A, 34B of the transition metal complex binding pair is a ligand; the linking moiety is a transition metal complex, and the transition metal complex is a second member of the transition metal complex binding pair; and the complex 60C' includes a hydrogel 68 having i) the transition metal complex (e.g., linking moiety 62B) attached thereto and ii) a plurality of primers 70, 70' attached thereto.

In further examples of this kit, the surface 32A, 32B, 32C is modified with the first member 34A, 34B of the transition metal complex binding pair; the first member 34A, 34B of the transition metal complex binding pair is a transition metal complex; the linking moiety 62B is a ligand, and the ligand is a second member of the transition metal complex binding pair; and the complex 60D' includes the metal nanoparticle 72 functionalized with i) the ligand (e.g., linking moiety 62B) and ii) the hydrogel 68 having a cluster of template nucleic acid strands 74 attached thereto.

Another example of a kit includes i) a flow cell 10, including: a flow channel 12; and a substrate 22E, 22F, 22G, 22H having a surface 52A, 52B, 52C, 52D that is at least partially exposed to the flow channel 12, the surface 52A, 52B, 52C, 52D being modified with a visible light responsive first member 54A, 54B of a transition metal complex binding pair; and ii) a flow cell surface chemistry fluid, including: a liquid carrier (e.g., fluid 76); and a complex 60C", 60D", 60F including a linking moiety 62C that is to chemically attach to the visible light responsive first member 54A, 54B and that is to desorb from the visible light responsive first member 54A, 54B when exposed to visible light.

Sequencing System

Figure 10:
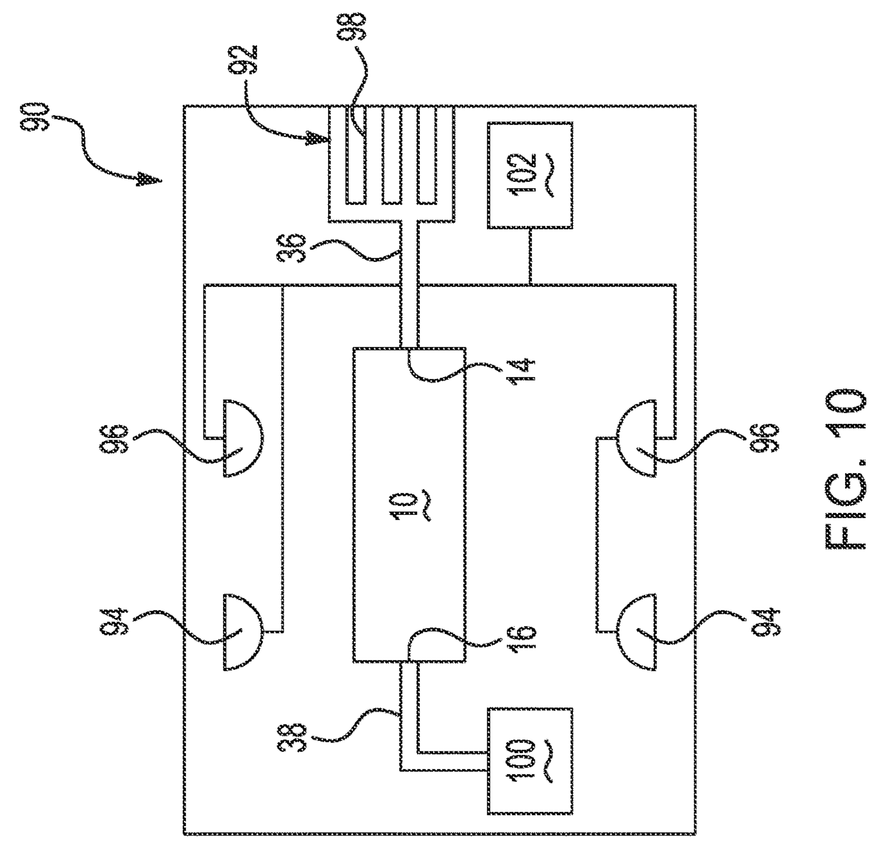
FIG. 10 is a schematic illustration of a sequencing system disclosed herein.

Any example of the flow cell 10 described herein may be part of a sequencing system. An example sequencing system 90 is shown schematically in FIG. 10. The sequencing system 90 includes a flow cell 10 including a regenerable surface (e.g., 32A, 32B, 32C, 52A, 52B, 52C, 52D) that is switchable, electrochemically or via visible light exposure, from a sequencing ready state to a sequencing unready state; a fluidic control system 92 including delivery fluidics to deliver a fluid to the flow cell 10; an illumination system 94 positioned to illuminate the regenerable surface (e.g., 32A, 32B, 32C, 52A, 52B, 52C, 52D); a detection system 96 positioned to capture an image of the regenerable surface (e.g., 32A, 32B, 32C, 52A, 52B, 52C, 52D); and a controller 102 to: cause electrodes 24A, 24B, 24C of the flow cell 10 to induce the sequencing unready state; or cause the illumination system 94 to expose the flow cell 10 to visible light.

The "sequencing ready state" is the state in which the surface chemistry is attached to form any example of the temporarily modified surface. In other words, this state refers to the condition of the flow cell 10 when surface chemistry for a desired nucleic acid analysis has been attached to the surface. In the sequencing ready state, the flow cell 10 is able to be used in a sequencing operation or another nucleic acid analysis. The "sequencing unready state" is the state in which the surface chemistry is not attached to the regenerable surface (e.g., 32A, 32B, 32C, 52A, 52B, 52C, 52D). In other words, this state refers to the condition of the flow cell 10 when surface chemistry for a desired nucleic acid analysis has not been attached to the surface. In the sequencing unready state, the flow cell 10 is not able to be used in a sequencing operation or another nucleic acid analysis due to the lack of suitable surface chemistry.

The fluidic control system 92 includes the inlet fluidics 36 and the outlet fluidics 38 as described herein. The inlet fluidics 36 may include fluid reservoirs or fluid cartridges 98 and fluid lines that supply the desired fluids, e.g., 76, 78, wash fluids, etc. to the flow cell 10 through the inlet 14. The outlet fluidics 38 may include a waste reservoir 100 and fluid lines that remove the fluids, e.g., 76, 78, wash fluids, etc. from the flow cell 10 through the outlet 16. The fluidic control system 92 may include pumps, valves, etc. to move the fluids in a desirable manner in response to commands from the controller 102. One specific example of the sequencing system 90 includes a reservoir fluidly connected to the delivery fluidics; and the fluid (e.g., first fluid 76) contained in the reservoir, wherein the fluid includes a complex 60A, 60B, etc. having a linking moiety 62A, 62B, etc. that is to chemically attach the complex 60A, 60B, etc. to the regenerable surface.

The illumination system 94 may be any light source (e.g., laser) that is capable of emitting the excitation wavelengths (e.g., ultraviolet light) for nucleic acid analysis. In some examples, the illumination system 94 includes another light source that is capable of emitting visible light for initiating substrate surface 52A, 52B, 52C, 52D regeneration. The illumination system is operable in response to commands from the controller 102.

The detection system 96 may be any detector that is capable of registering the emission photons resulting from the nucleic acid analysis and produces a recordable output. In some examples, the detection system 96 is a digital imaging system. The detection system 96 operates in response to commands from the controller 102.

The controller 102 may include any processor-based or microprocessor based system, including systems using microcontrollers, reduced instruction set computers (RISC), application specific integrated circuits (ASICs), field programmable gate array (FPGAs), logic circuits, and any other circuit or processor that can execute functions described herein. While several examples have been provided, it is to be understood that these are not intended to limit in any way the definition and/or meaning of the term system controller. In an example, the system controller 102 executes a set of instructions that are stored in one or more storage elements, memories, or modules in order to deliver fluids, apply voltage biases, operate the illumination system 94, operate the detection system 96, etc. in accordance with the examples set forth herein. In examples including the electrochemically regenerable surface 32A, 32B, 32C, controller 102 may also include a potentiostat to control the desired bias between the working electrode(s) 24A, 24B, 24C and the counter electrode 40 and/or between the second working electrode(s) 42A, 42B, 42C and the counter electrode 40.

In one example of the sequencing system 90, the regenerable surface is a working electrode surface 24A, 24B, 24C; and the working electrode surface 24A, 24B, 24C is modified with a first member 34A, 34B of a transition metal complex binding pair in the sequencing unready state.

In another example of the sequencing system 90, the regenerable surface is a working electrode surface 24A, 24B, 24C; and the working electrode surface 24A, 24B, 24C is unmodified in the sequencing unready state.

In another example of the sequencing system 90, the regenerable surface is a substrate surface 52A, 52B, 52C; and the substrate surface 52A, 52B, 52C is modified with a visible light responsive first member 54A, 54B of a transition metal complex binding pair in the sequencing unready state.

ADDITIONAL NOTES

It is to be understood that any features of the examples set forth herein may be combined together in any desirable manner to achieve the benefits as described in this disclosure, including, for example, to obtain a flow cell.

It should also be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

While several examples have been described in detail, it is to be understood that the disclosed examples may be modified. Therefore, the foregoing description is to be considered non-limiting.

What is claimed is:

1. A method, comprising:

introducing a first fluid to a flow channel of a flow cell including a working electrode having an unmodified surface that is at least partially exposed to the flow channel, wherein a complex present in the first fluid includes a linking moiety and an orthogonal functional group that does not attach to the unmodified surface, wherein the linking moiety chemically attaches the complex to the surface to form a temporarily modified surface of the working electrode and wherein the orthogonal functional group is biotin;

introducing, into the flow channel, a second fluid including a hydrogel having i) a plurality of primers attached thereto and ii) a reactive functional group attached thereto that is reactive with the orthogonal functional group, wherein the reactive functional group is streptavidin; and performing a sensing operation involving the complex of the temporarily modified surface, wherein the sensing operation involves:

amplifying a template nucleic acid strand using the plurality of primers to generate a cluster of template nucleic acid strands;

introducing, into the flow channel, a third fluid including a plurality of optically labeled nucleotides; and optically detecting an incorporation event of a respective one of the plurality of optically labeled nucleotides into a nascent strand along at least some of the template nucleic acid strands; and applying a desorption voltage of the linking moiety to the working electrode, thereby detaching the linking moiety and regenerating the surface.

2. The method as defined in claim 1, wherein applying the desorption voltage involves applying a negative bias to the working electrode.

3. The method as defined in claim 2, further comprising introducing a wash fluid to the flow channel after the desorption voltage is applied.

4. The method as defined in claim 1, wherein applying the desorption voltage involves applying a positive bias to the working electrode.

5. The method as defined in claim 1, wherein:

the flow cell includes:

a substrate;

the working electrode positioned over the substrate;

a patterned insulating material positioned over the working electrode, the patterned insulating material defining depressions separated by interstitial regions, wherein the unmodified surface is exposed at each of the depressions; and a second working electrode positioned over the interstitial regions; and the method further comprises applying a desorption voltage of the linking moiety to the second working electrode as the first fluid is introduced, thereby repelling the complex from the interstitial regions.

6. The method as defined in claim 5, further comprising applying the desorption voltage of the linking moiety to the second working electrode after the sensing operation.

7. A method, comprising:

introducing a first fluid to a flow channel of a flow cell including a surface of a substrate that is at least partially exposed to the flow channel, the surface being modified with a visible light responsive first member of a transition metal complex binding pair, whereby a linking moiety of a complex present in the first fluid chemically attaches the complex to the surface to form a temporarily modified surface of the substrate;

performing a sensing operation involving the complex of the temporarily modified surface, wherein the sensing operation involves nucleic acid sequencing and optical detection; and exposing the temporarily modified surface to visible light, thereby detaching the linking moiety and regenerating the surface.

8. The method as defined in claim 7, wherein:

the linking moiety is a thioether; and the complex is a hydrogel having i) the thioether attached thereto and ii) a plurality of primers attached thereto.

9. The method as defined in claim 7, wherein:

the linking moiety is a thioether; and the complex is a hydrogel having i) the thioether attached thereto and ii) a cluster of template nucleic acid strands attached thereto.

* * * * *